US008808650B1

(12) United States Patent
Iqbal et al.

(10) Patent No.: US 8,808,650 B1
(45) Date of Patent: Aug. 19, 2014

(54) FOLDABLE SPECIMEN RACK WITH CONFIGURABLE SPECIMEN RECEIVER

(71) Applicant: Shazi Iqbal, Danville, CA (US)

(72) Inventors: Shazi Iqbal, Danville, CA (US); Shiraz Iqbal, Carrollton, TX (US); Merrill S Ross, II, New Lebanon, NY (US); Jeffrey S Ross, Lebanon Springs, NY (US); Shahin Iqbal, Flower Mound, TX (US)

(73) Assignee: Shazi Iqbal, Danville, CA (US)

( * ) Notice: Subject to any disclaimer, the term of this patent is extended or adjusted under 35 U.S.C. 154(b) by 10 days.

(21) Appl. No.: 13/844,300

(22) Filed: Mar. 15, 2013

(51) Int. Cl.
*B01L 9/06* (2006.01)

(52) U.S. Cl.
CPC ....................... *B01L 9/06* (2013.01)
USPC ......................... 422/562; 422/564

(58) Field of Classification Search
CPC .................. B01L 9/06; B01L 9/543

USPC .......................... 422/560–562, 564
See application file for complete search history.

(56) References Cited

U.S. PATENT DOCUMENTS

| 1,021,998 | A | * | 4/1912 | Myers ........................... 206/443 |
| 3,390,783 | A | * | 7/1968 | Quackenbush, Jr. ............ 211/73 |
| 3,682,597 | A | * | 8/1972 | Husch ........................... 422/408 |
| 5,057,282 | A | * | 10/1991 | Linder .......................... 422/547 |
| 5,143,210 | A | * | 9/1992 | Warwick et al. .............. 206/738 |
| 5,685,438 | A | * | 11/1997 | Emanuel et al. ............. 211/70.1 |
| 5,725,109 | A | * | 3/1998 | Moulton et al. ................ 211/73 |

\* cited by examiner

*Primary Examiner* — Paul Hyun
(74) *Attorney, Agent, or Firm* — Mark P Kahler

(57) ABSTRACT

A foldable specimen rack includes a foldable box that moves from a closed, storage position to an open in-use position. The foldable box may include and open box and open bottom when the box is in the open position. The foldable specimen rack may also include a removable insert member situated adjacent the open top of the foldable box. The removable insert member includes multiple specimen holder receiving slots. Different removable insert members may includes slots that accommodate different size specimen holders.

16 Claims, 23 Drawing Sheets

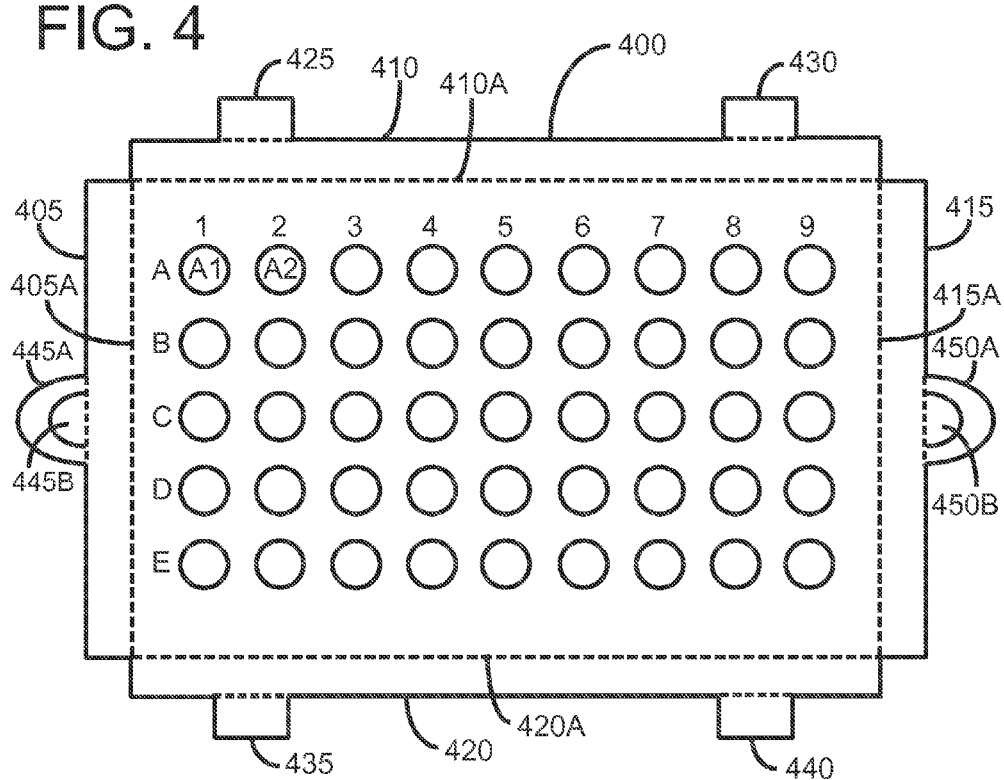
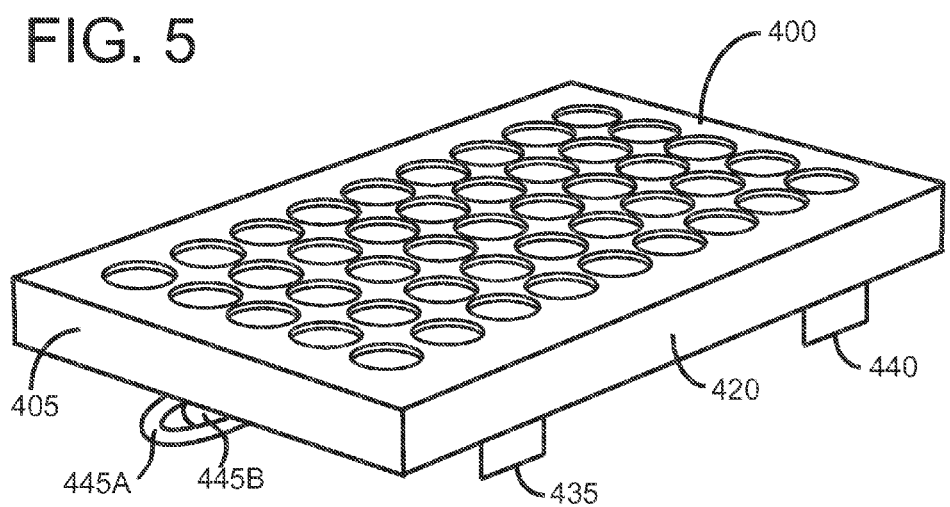

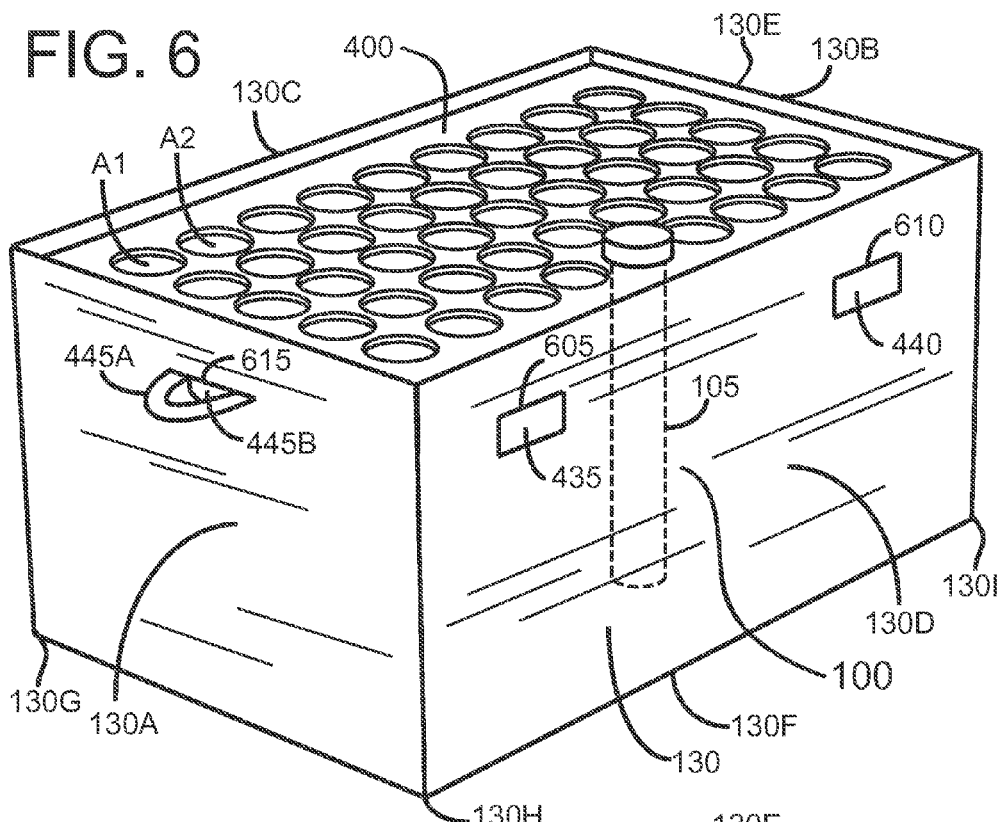
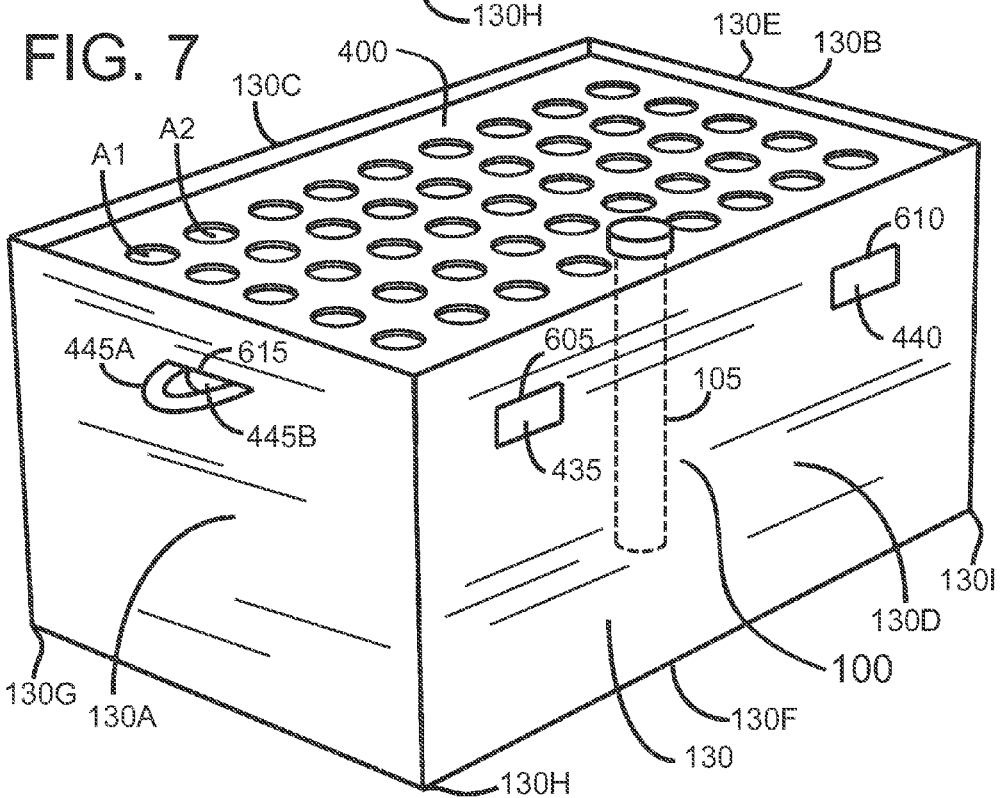

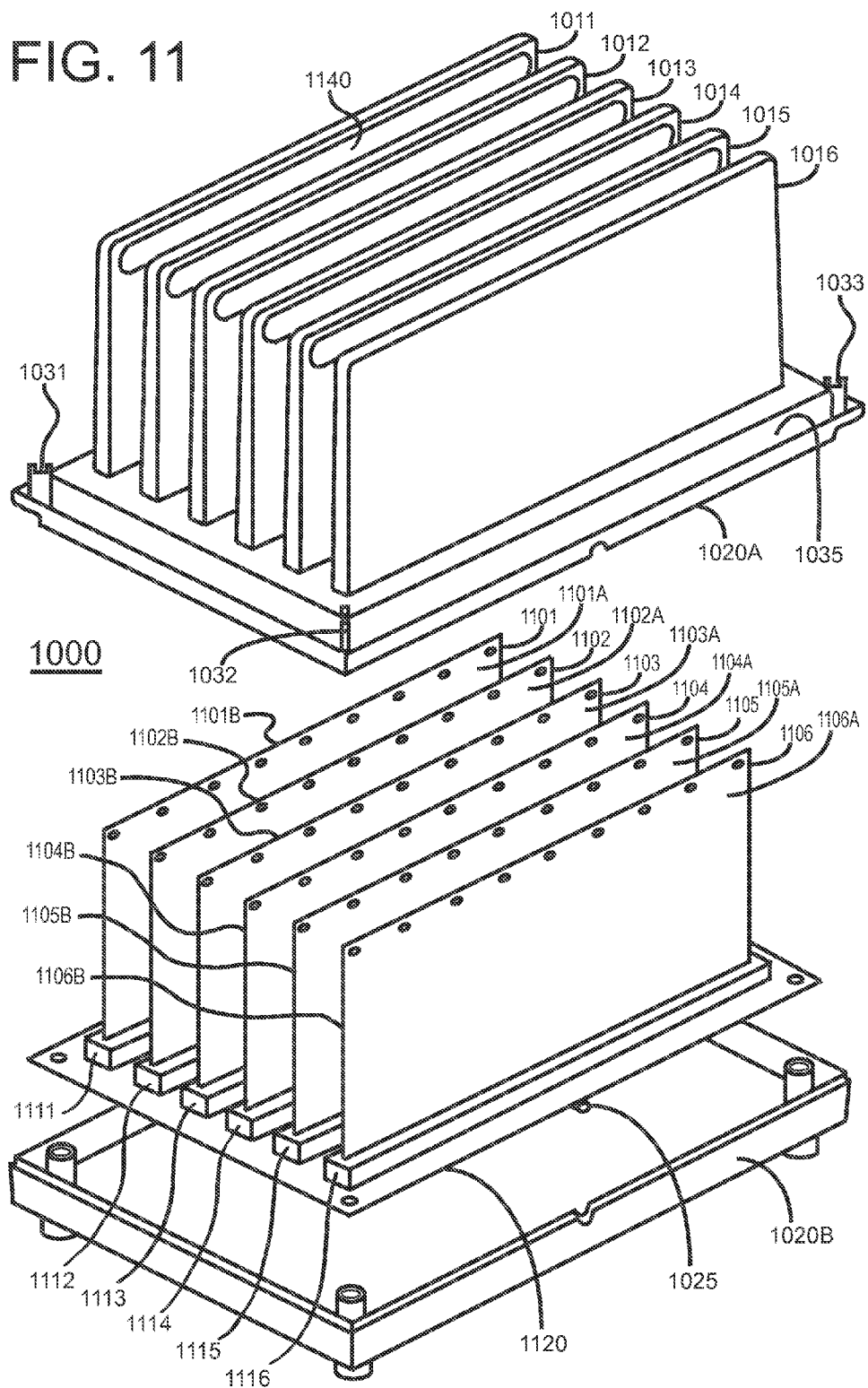

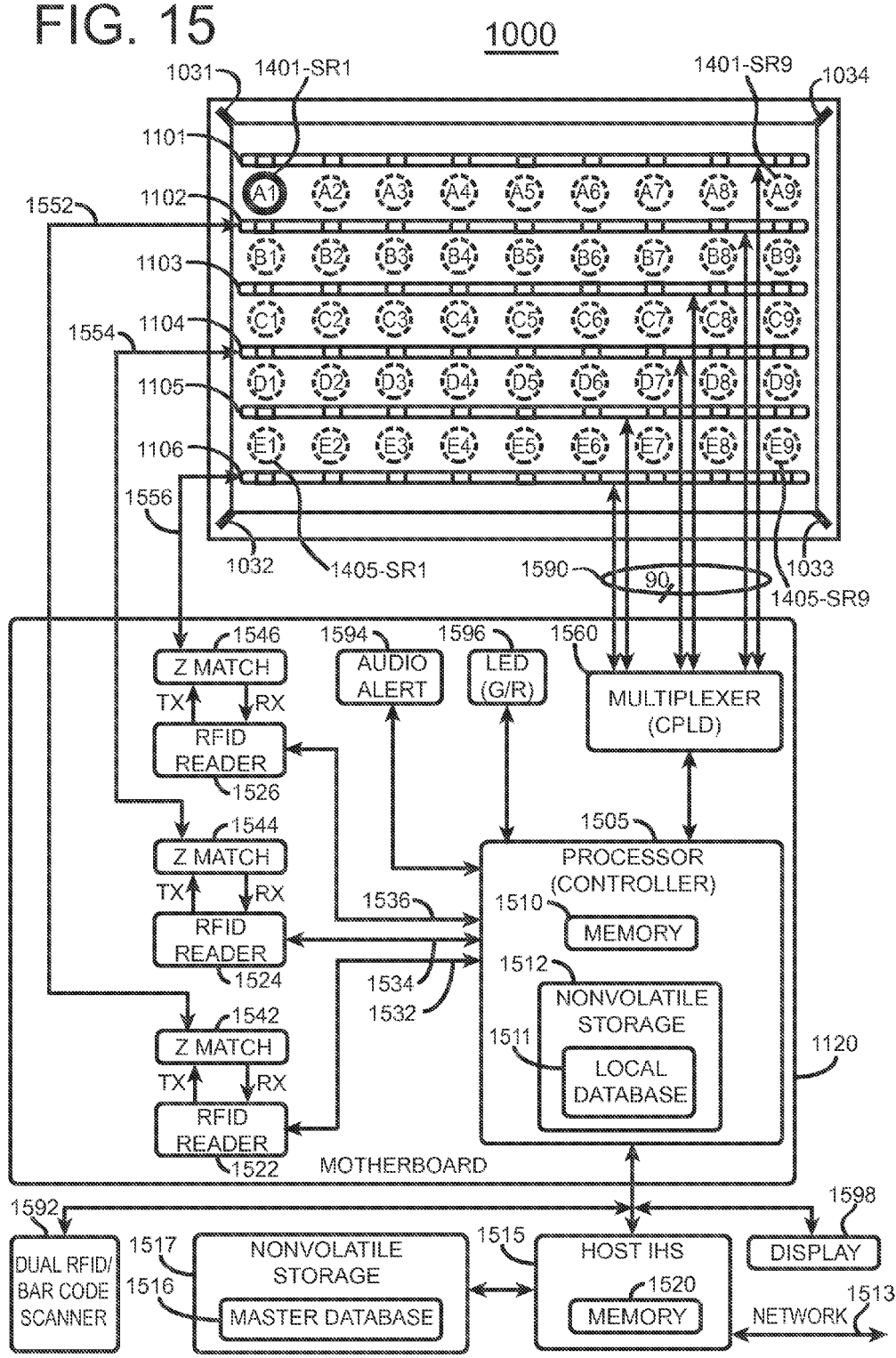

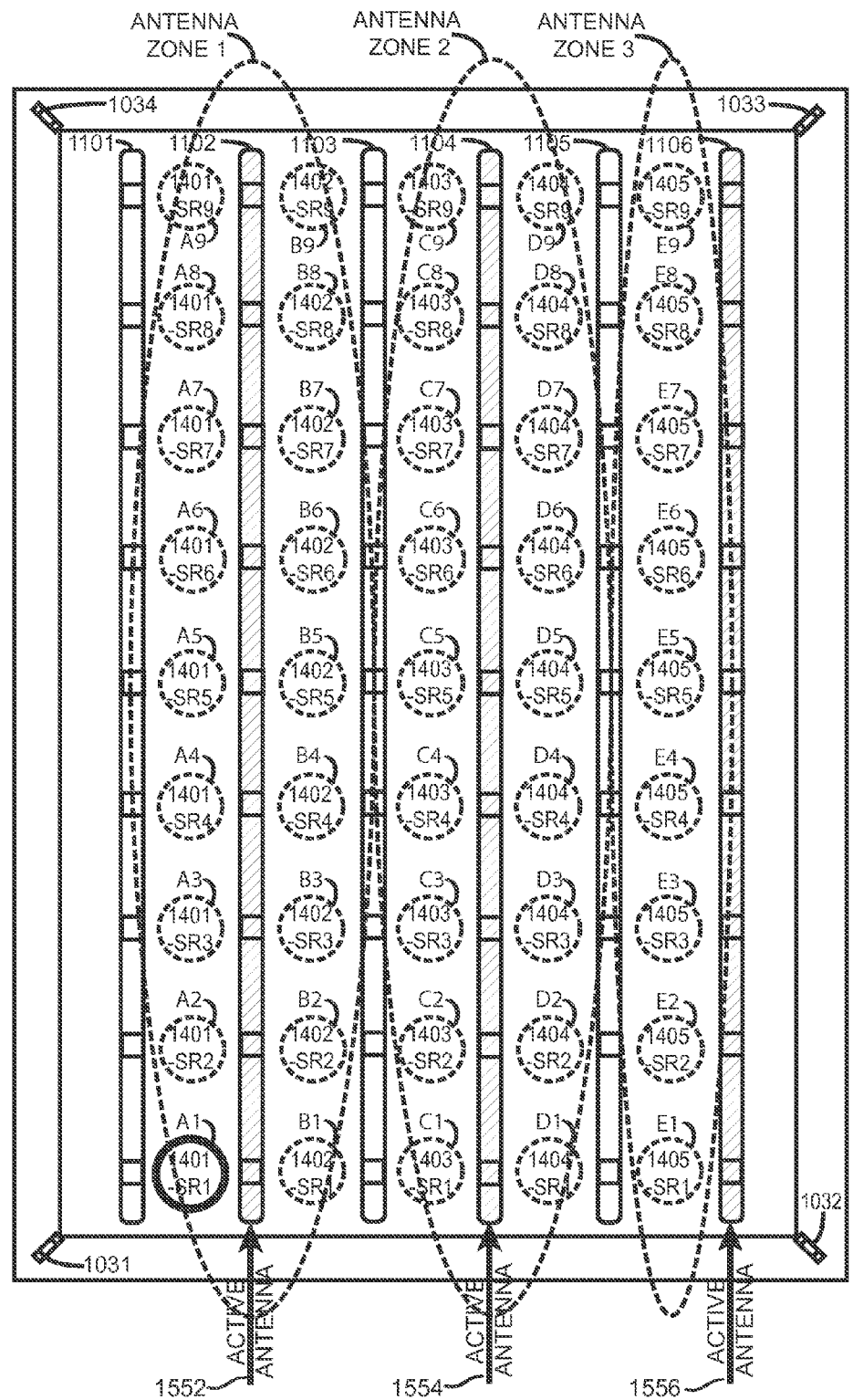

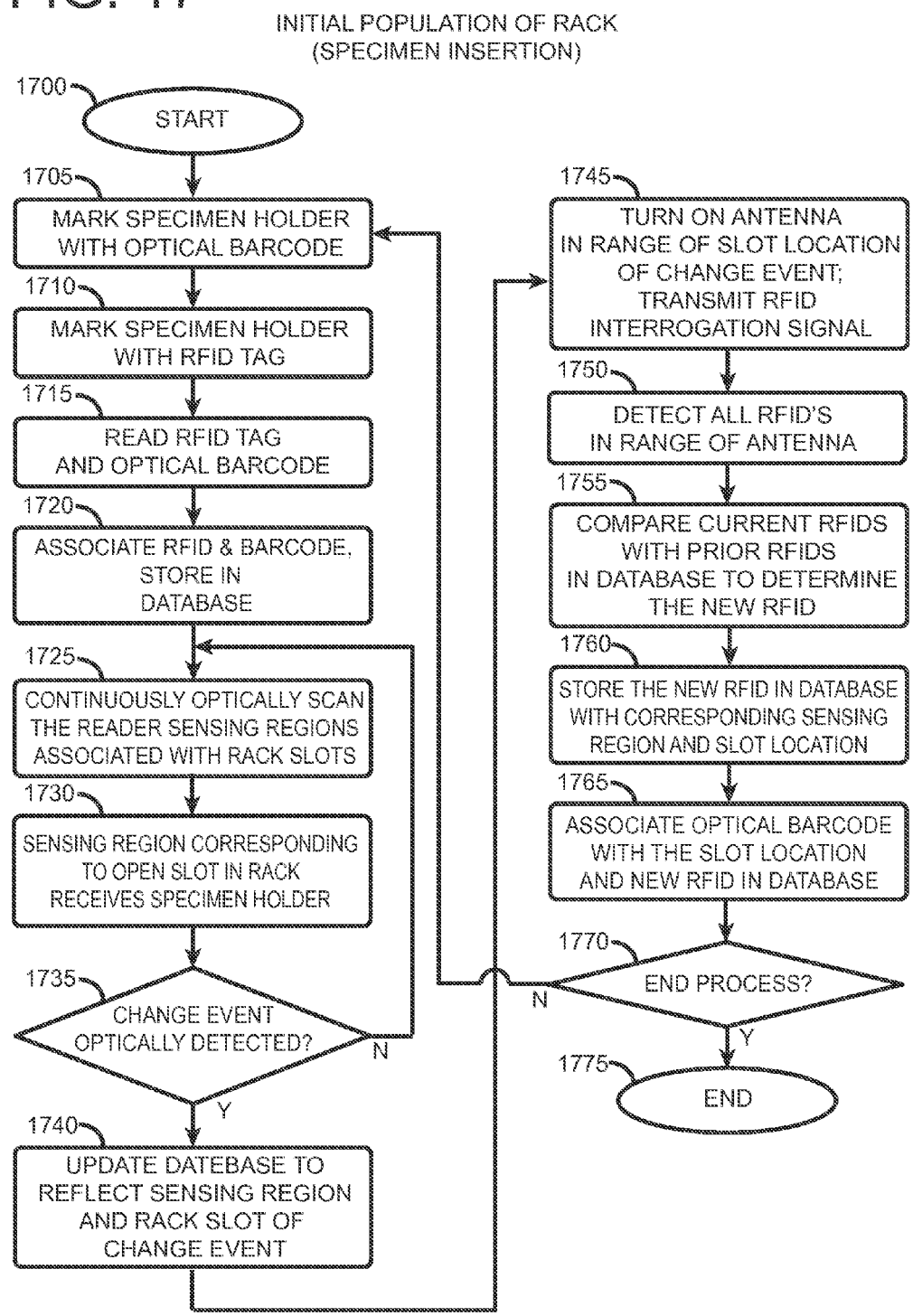

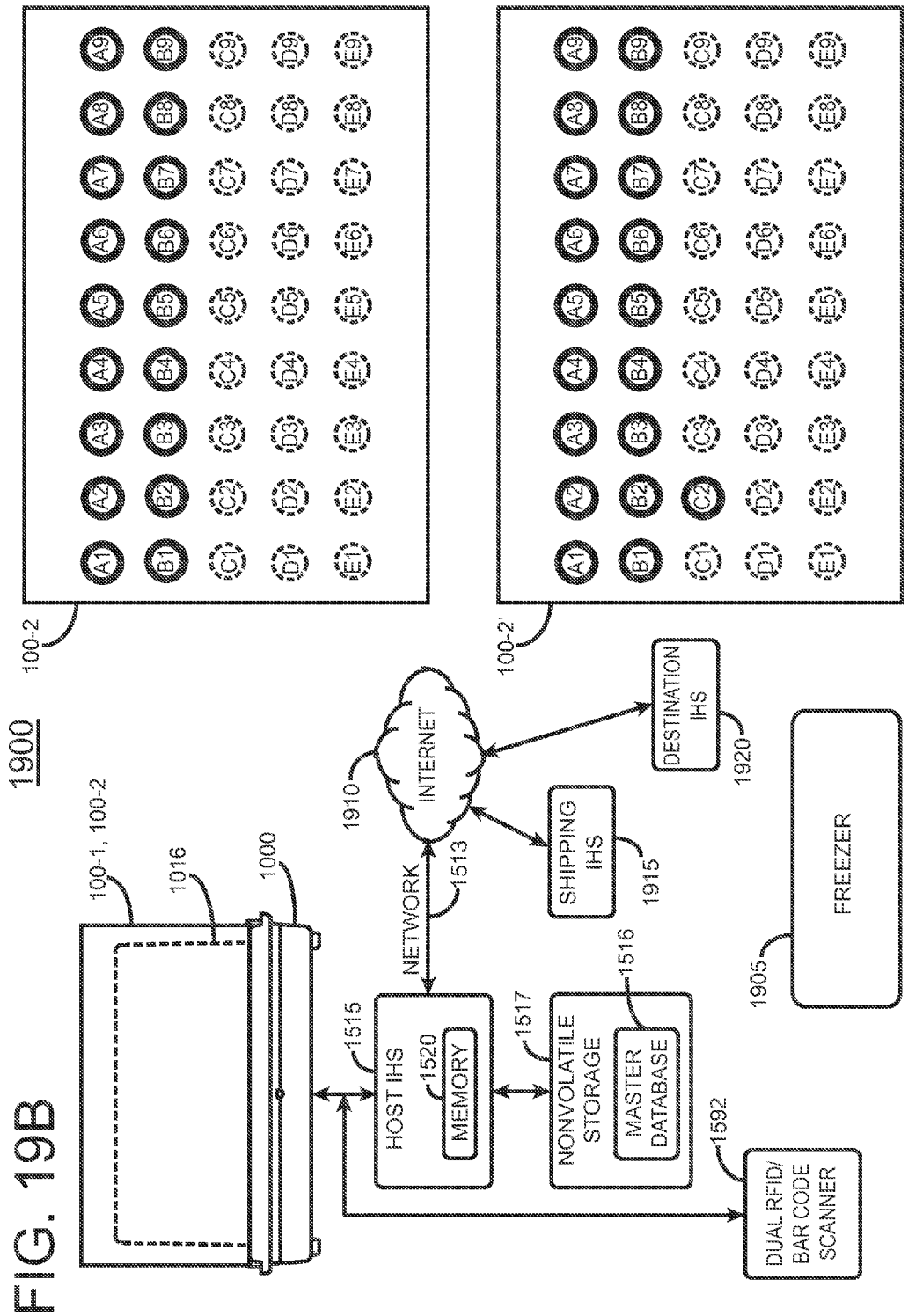

FOLDABLE SPECIMEN RACK WITH CONFIGURABLE SPECIMEN RECEIVER

BACKGROUND

The disclosures herein relate generally to specimen handling, and more specifically, to storage and/or management of medical specimens and other specimens.

In fields such as medicine, chemistry and other arts, it is often helpful to store a specimen, i.e. a sample of a particular substance or material, in a container for later use. Before or after placing the specimen in the container, a technician or other user may mark the container with a label to identify the specimen. The user typically sends the container off to storage with other similar containers. The user may retrieve the container and specimen at a later time by locating the container via its identification label.

BRIEF SUMMARY

In one embodiment, a specimen rack includes a foldable box that is moveable between an open position and a closed position, the foldable box including an open top and an open bottom when the foldable box is in the open position. The specimen rack also includes a removable insert member situated adjacent the open top of the foldable box when the foldable box is in the open position, the removable insert member including a plurality of specimen holder receiving slots for receiving specimen holders for specimen storage.

In another embodiment, a method of assembling a specimen rack includes providing a foldable box that is moveable between a closed open position and a position, the foldable box including an open top and an open bottom when the foldable box is in the open position. The method also includes moving the foldable box from the closed position to the open position. The method further includes attaching a removable insert member adjacent the open top of the foldable box when the foldable box is in the open position, the removable insert member including a plurality of specimen holder receiving slots for receiving specimen holders for specimen storage.

In one embodiment, the removable insert member includes a plurality of tabs that fit in a plurality of corresponding apertures in the foldable box to support the removable insert member in the foldable box. The method includes inserting the plurality of tabs respectively in the plurality of apertures of the foldable box.

BRIEF DESCRIPTION OF THE DRAWINGS

The appended drawings illustrate only exemplary embodiments of the invention and therefore do not limit its scope because the inventive concepts lend themselves to other equally effective embodiments.

FIG. 4 is a top view of the removable insert member of the disclosed specimen rack before assembly of the removable insert member.

FIG. 5 is a top view of the removable insert member of the disclosed specimen rack after assembly of the removable insert member.

FIG. 6 is a perspective view of the disclosed specimen rack that includes a removable insert member for receiving specimen holders of a particular size.

FIG. 7 is a perspective view of the disclosed specimen rack that includes a removable insert member that receives specimen holders of a size that is different from the size that the specimen rack of FIG. 7 accommodates.

FIG. 11 is an exploded perspective view of the disclosed specimen reader.

FIG. 15 is high level block diagram of the disclosed specimen reader.

FIG. 16B is a top view of the disclosed specimen reader after populating the specimen rack with one specimen holder.

FIG. 17 is a flowchart of the disclosed process for initially populating the disclosed specimen rack on the specimen reader.

FIG. 19B is a block diagram of one embodiment of the specimen holder tracking system that illustrates specimen insertion into a specimen rack.

DETAILED DESCRIPTION

The disclosed specimen reader apparatus and methodology provides a convenient and reliable way of tracking specimens when specimen holders are added to, or removed from, the disclosed specimen rack. In one embodiment, the specimen reader receives a specimen rack that includes specimen holder receiving slots for receiving respective specimen holders. Each specimen holder may include a radio frequency identifier (RFID) tag and an optical barcode that are unique to that particular specimen holder. The user places the specimen rack on the specimen reader before populating the specimen rack with specimen holders.

After the specimen reader receives the specimen rack, the user may start to populate the specimen holder receiving slots of the specimen rack. In one embodiment, the user may place specimen holders in the specimen rack, one specimen holder at a time. The specimen reader includes an optical detector apparatus that scans the specimen holder receiving slots to detect a change event. A change event may be the insertion of a specimen holder at a particular specimen holder receiving slot where there was no specimen holder before, or the removal of a specimen holder from a particular specimen holder receiving slot. In response to the change event, a radio frequency (RF) transmitter in the specimen reader transmits an RFID interrogation signal to the specimen holders in the specimen rack. The specimen holders receive the RFID interrogation signal and in response transmit respective RFIDs back to the specimen reader. The specimen reader receives these RFIDs, thus providing currently received RFIDs. The specimen reader may compare the currently received RFIDs with RFIDs received on a previous scan to determine the RFID of a newly inserted specimen holder that caused the change event.

In one embodiment, the disclosed specimen rack includes an inner foldable box that opens to form a rectangular tube with and an open region at the top of the box and an open region at the bottom of the box. A removable insert member is attached to the inner foldable box in the open region adjacent the top of the inner foldable box. The removable insert member includes openings that form specimen holder receiving slots within the insert member. Each opening in the removable insert member, together with a specimen holder receiving region below the opening, cooperate to form a specimen holder receiving slot. Different insert members may include openings of different sizes to accommodate different size specimen holders. The specimen rack may further include an outer box, i.e an outer sleeve, into which the inner foldable box slides to protect specimen holders in the specimen holder receiving slots. The user may remove the outer box before placing the specimen rack on the specimen reader.

Figure 1:
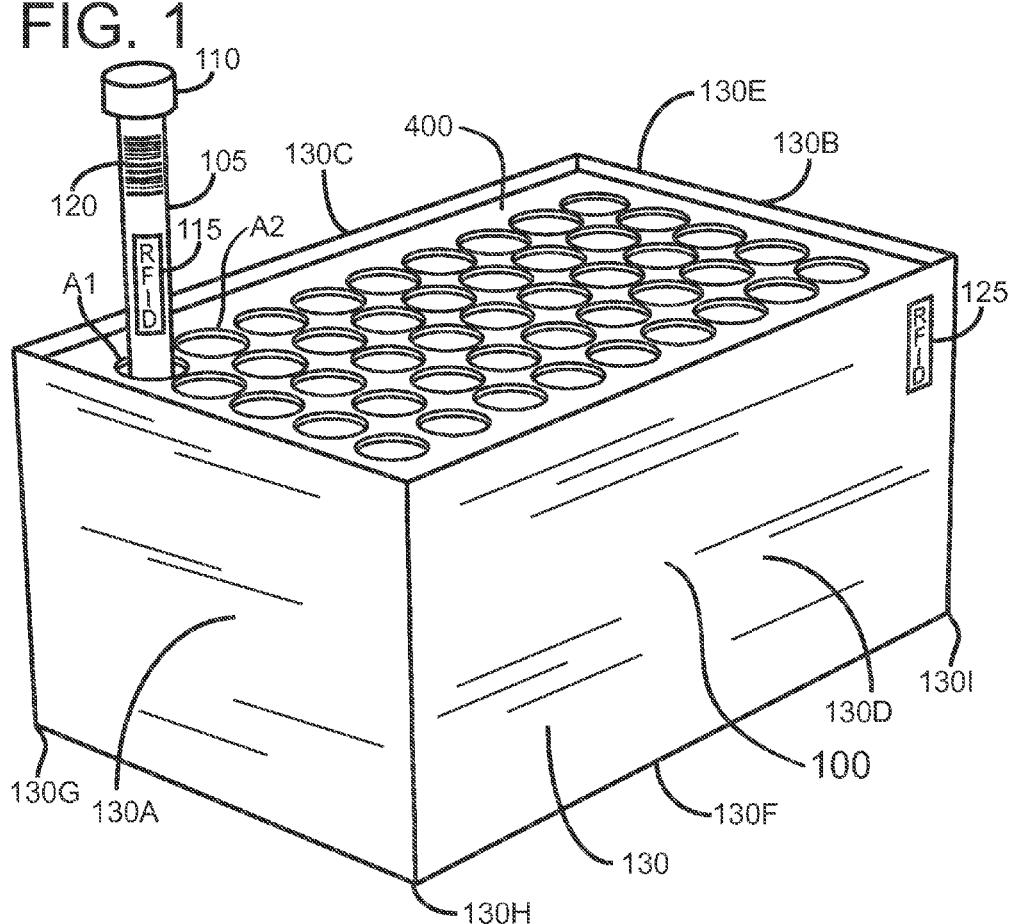
FIG. 1 is a perspective view of one embodiment of the disclosed specimen rack.

FIG. 1 shows a perspective view of a specimen rack 100 that stores specimen holders such as specimen holder 105. Specimen holder 105 includes a removable cap 110 at the top of the specimen holder 105 to seal a specimen in a chamber within specimen holder 105. Specimen holder 105 includes a unique RFID tag 115 and a unique barcode 120. More particularly, RFID tag 115 stores an RFID that is unique to a particular specimen holder 105. The barcode 120 represents a barcode ID that is unique to the particular specimen holder 105. In one embodiment, specimen rack 100 may includes an RFID tag 125 that stores an RFID that is unique to specimen rack 100.

Figure 2:
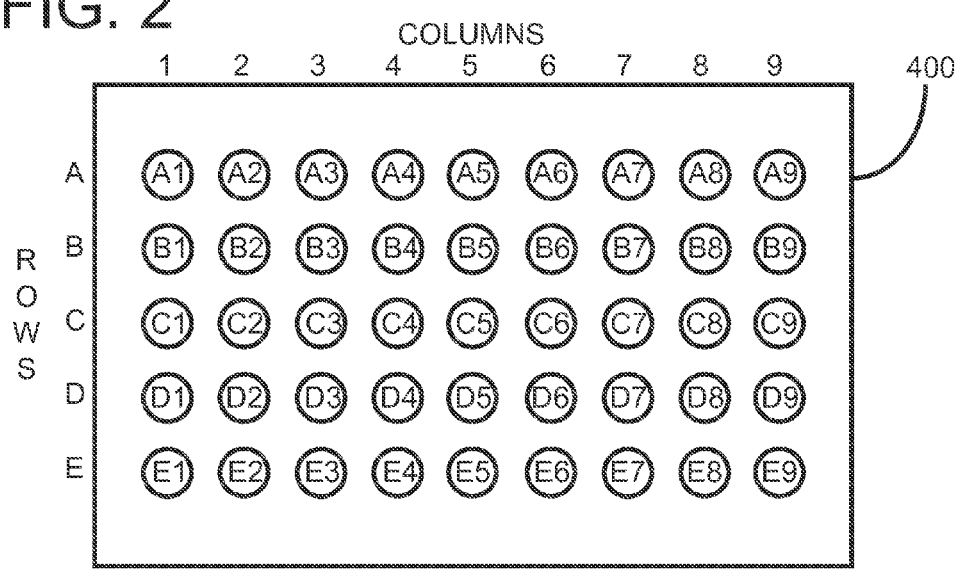
FIG. 2 is a top view of the disclosed specimen rack.

Specimen rack 100 includes a four-sided foldable box 130 that includes opposed sides 130A, 130B and opposed sides 130C, 130D. Box 130 is open at top 130E and bottom 130F to form a rectangular tube when unfolded, as shown in FIG. 1. A removable insert member 400 is attached to box 130 adjacent top 130E. The insert member 400 is spaced sufficiently below top 130E to allow for clearance of the specimen holders 105 that the specimen rack 100 stores. In one embodiment of specimen rack 100, insert member 400 includes multiple specimen holder receiving slots, wherein each slot is formed by an opening and a specimen holder receiving region below the opening. Insert member 400 may arrange the specimen holder receiving slots in an array of rows and columns, such as rows A, B, C, D, E and columns 1-9, as shown in the top view of insert member 400 in FIG. 2. Slot A1 (row A, column 1) and slot A2 (row A, column 2) are representative of the specimen holder receiving slots of insert member 400. Slot A1 and slot A2 open into respective specimen holder receiving regions (not separately numbered) below these slots. In this particular example, the arrangement of 5 rows and 9 columns of slots accommodates forty five (45) specimen holders 105. Those skilled in the art will appreciate that the number of rows and columns in insert member 400 and the size of specimen rack 100 may vary to accommodate a greater or lesser number of specimen holders 105. While FIG. 1 illustrates RFID tag 125 as being situated on foldable box 130, RFID tag 125 may alternatively be situated on removable insert member 400.

Figure 3A:
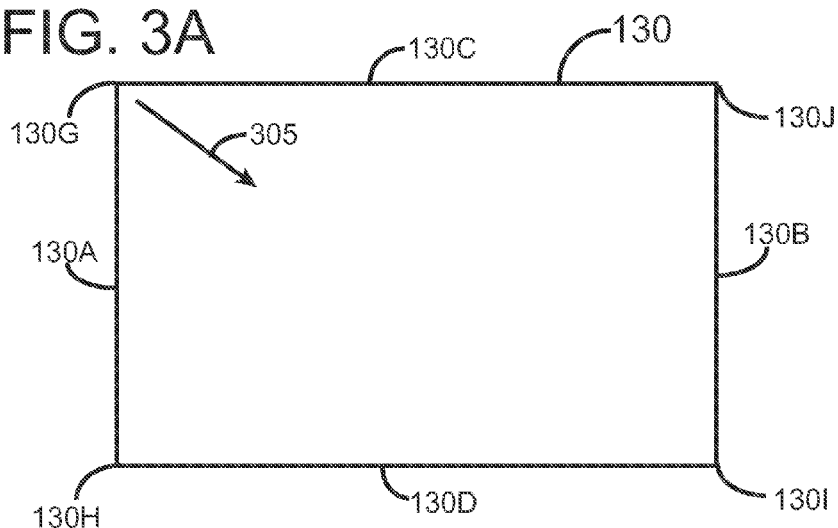
FIGS. 3A-3D are a series of views that show how the disclosed rack folds for storage or shipping.
Figure 3B:
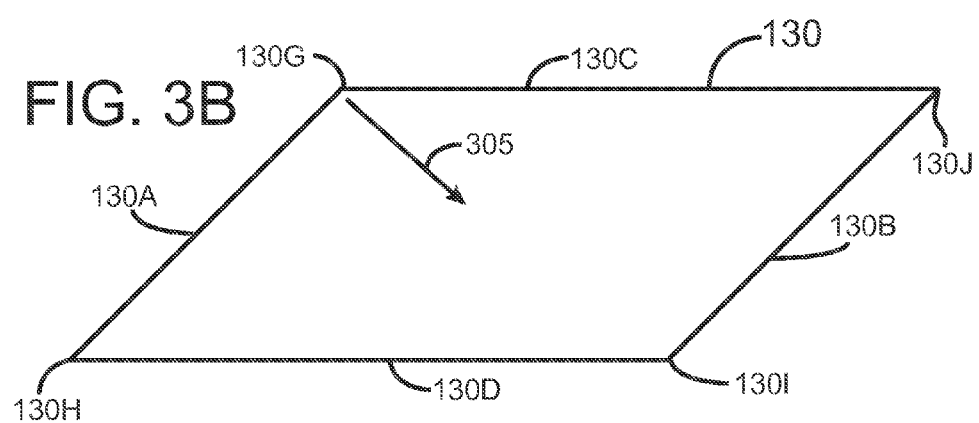
Figure 3C:
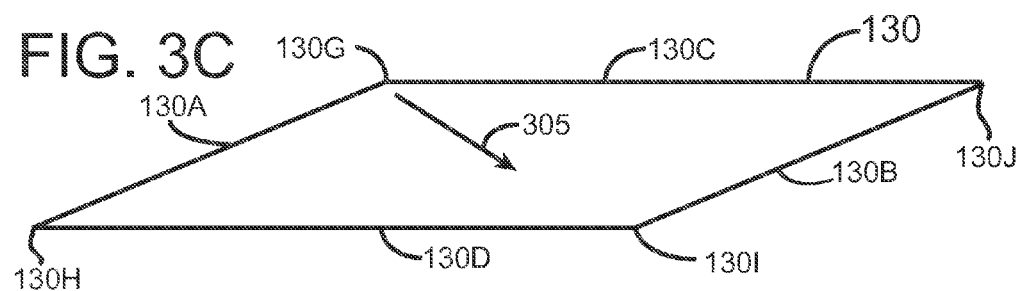
Figure 3D:
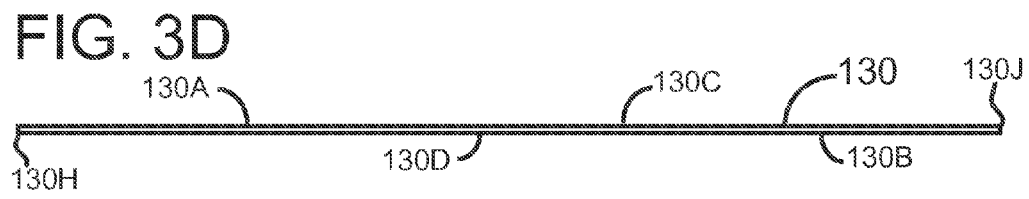

FIGS. 3A-3D show a progression of views that demonstrate how box 130 folds for storage and shipping. FIG. 3A shows box 130 in the all sides orthogonal, unfolded orientation, ready for installation of removable insert member 400. FIG. 3A depicts box 130 with four corners 130G, 130H, 130I and 130J. Foldable box 130 includes opposed corners 130G and 130I that fold toward one another as indicated by arrow 305. Folding continues as shown in FIG. 3B and FIG. 3C until reaching the totally folded orientation of FIG. 3D. Box 130 exhibits a parallelepiped geometry as it folds from the position of FIG. 3A to the position of FIG. 3B. In one embodiment, foldable box 130 is fabricated from chip board, card board stock or other foldable material with sufficient rigidity to support insert member 400 with specimen holders 105 therein.

FIG. 4 is a more detailed representation of removable insert member 400 prior to assembly. In one embodiment, removable insert member 400 is fabricated from a single piece of the same material as box 130, such as chip board or card board. A sheet of this material may be machine-cut to the geometry that FIG. 4 depicts. In FIG. 4, dashed lines indicate fold lines in insert member 400. Insert member 400 includes flaps 405, 410, 415 and 420 that fold downward along fold lines 405A, 410A, 415A and 420A to from the assembled insert member 400 that FIG. 5 depicts. Flap 410 includes tabs 425 and 430. Flap 420 includes tabs 435 and 440. A handle 445A and a handle inner flap 445B within handle 445A extend from flap 405, as shown in FIG. 4A. Similarly, a handle 450A and a handle inner flap 450B within handle 450A extend from flap 415, as shown in FIG. 4. Handle 445A and handle inner flap 445B together form a handle/insert support structure. Likewise, handle 450A and handle inner flap 450B together form another handle/insert support structure on the end of insert member 400 opposite the end on which handle 445A is situated. Before installing insert member 400 in foldable box 130, a user folds the insert member 400 along the dashed fold lines that FIG. 4 indicates to form the completely assembled insert member 400 that FIG. 5 depicts.

FIG. 6 shows specimen rack 100 after installation of removable insert member 400 adjacent open top 130E. Tabs 435 and 440 extend through slots 605 and 610, respectively, of side 130D of box 130. Likewise, tabs 425 and 430 extend through similar slots (not visible) of side 130C of box 130. Mounting the tabs 435, 440, 425 and 430 through the respective slots of box 130 in this manner provides support to removable insert member 400 within box 130 of specimen rack 100.

As seen in FIG. 6, handle 445A and handle inner flap 445B extend through a slot 615 in side 130A of box 130. Handle 445A extends in a direction generally normal to box side 130A so that the user may easily grasp handle 445A to move the specimen rack. Handle inner flap 445B is oriented parallel to, and in contact with box side 130A, with a layer of adhesive between inner flap 445B and box side 130A. More particularly, in one embodiment, a layer of removable adhesive (not shown) adhesively connects handle inner flap 445B to box side 130A. In a similar manner, another layer of removable adhesive connects handle inner flap 450B (not shown) to box side 130B at the opposed end of box 130. With the assembly of removable insert member 400 to box 130 in this manner, the user may easily grasp handles 445A and 450A to move specimen rack 100 to and from the specimen reader.

FIG. 7 shows the specimen rack 100 after the user replaces or otherwise installs a removable insert member 400 that includes smaller slots, such as slots A1 and A2, than those of insert member 400 of FIG. 6. In this manner, the specimen rack may accommodate different size sample holders 105.

Figure 8:
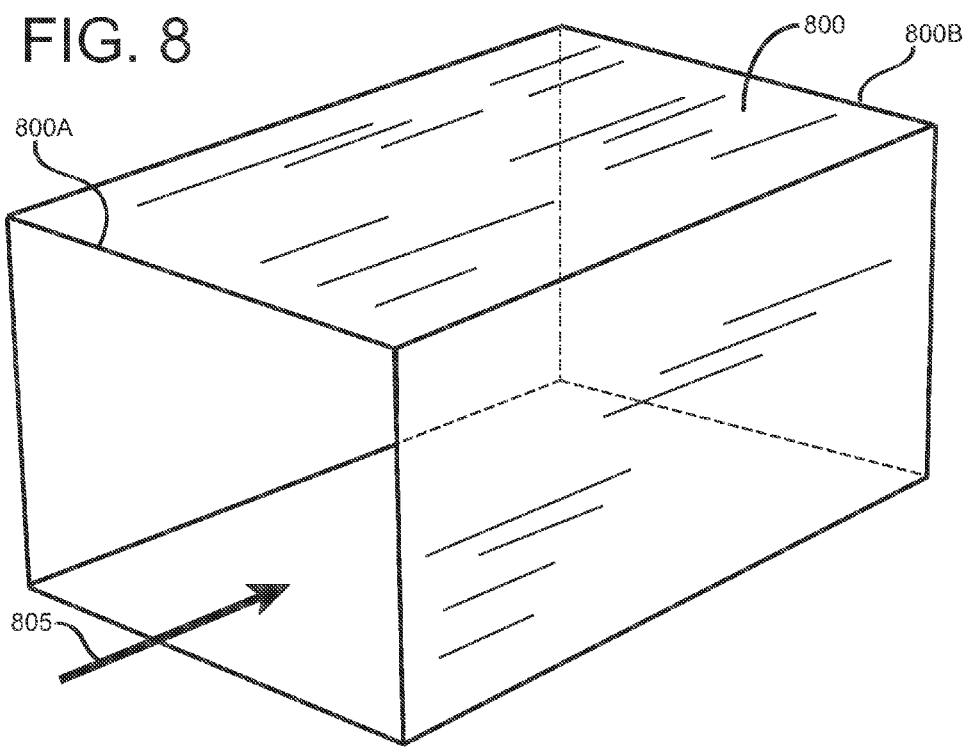
FIG. 8 is a perspective view of a sleeve that fits over the specimen rack to protect the specimen rack.
Figure 9:
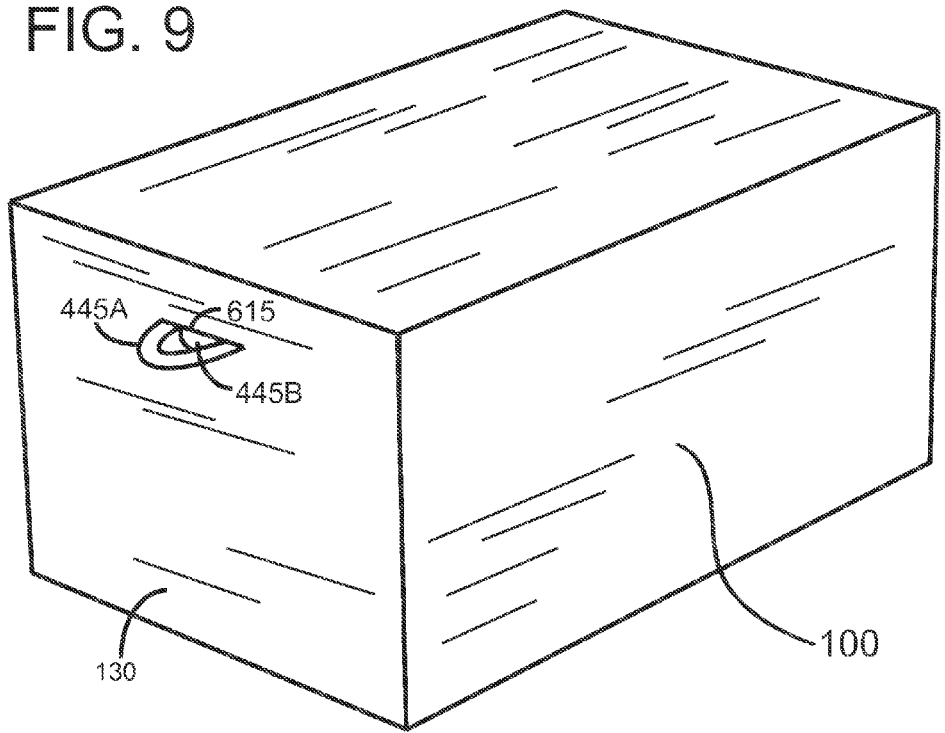
FIG. 9 is a perspective view of the disclosed specimen rack with the sleeve of FIG. 8 installed thereon.

FIG. 8 shows a protective sleeve 800 that slides over the assembled box 130 and insert member 400 to form a covered specimen rack 100. Sleeve 800 includes opposed open ends 800A and 800B. Protective sleeve may be fabricated from the same material as box 130. The user typically slides protective sleeve 800 in the direction of arrow 805 over the box 130 and insert member 400 to form the covered specimen rack 100 of FIG. 9.

Figure 10A:
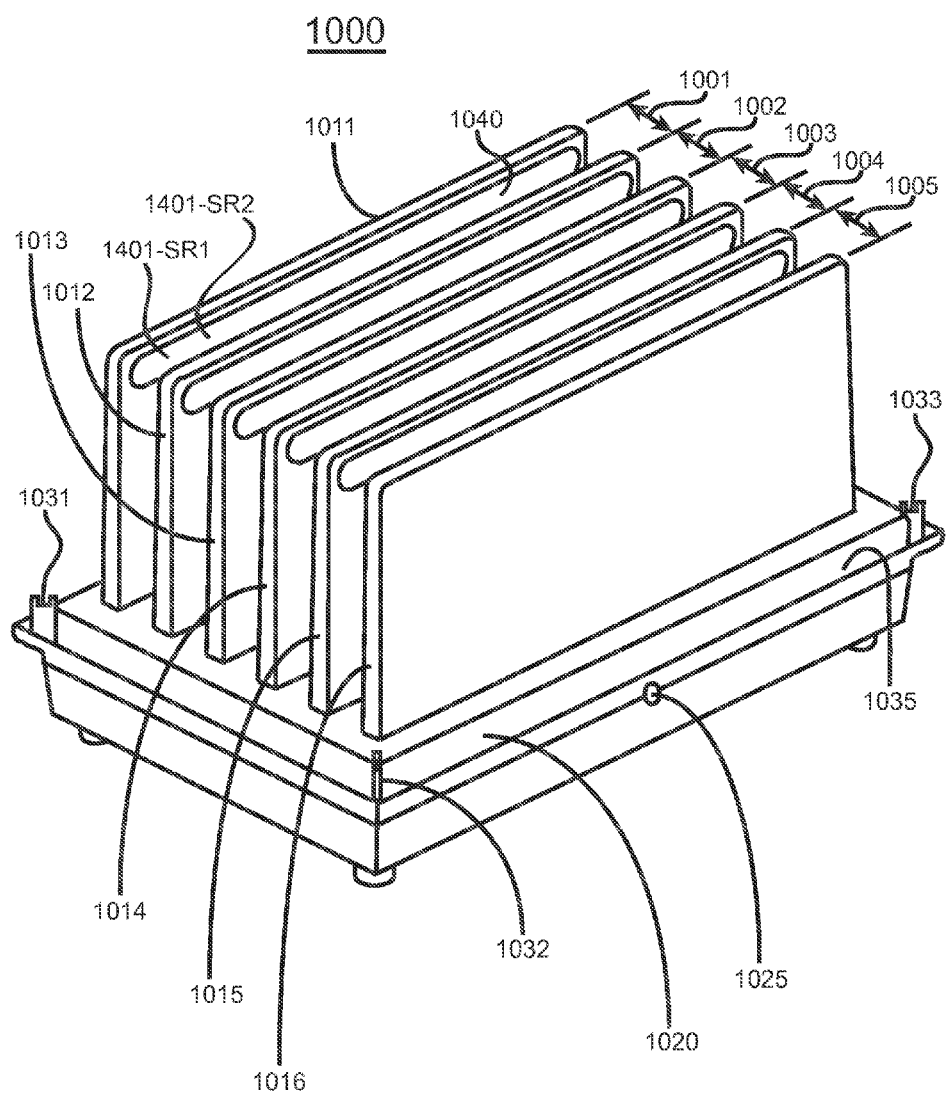
FIG. 10A is a perspective view of the disclosed specimen reader before placement of the specimen rack thereon.

FIG. 10A shows a perspective view of one embodiment of the disclosed specimen reader 1000. Specimen reader 1000 includes sensing bays 1001, 1002, 1003, 1004 and 1005. Each of these sensing bays includes multiple sensing regions, as discussed in more detail below. FIG. 10A shows two of the nine sensing regions that sensing bay 1001 includes, namely sensing region 1401-SR1 and adjacent sensing region 1401-SR2. FIG. 14D, which is discussed in more detail below, shows all sensing regions of one embodiment of specimen reader 1000. In the particular embodiment that FIG. 10A depicts, specimen reader 1000 includes substantially rectangular sensor housings 1011, 1012, 1013, 1014, 1015 and 1016.

Specimen reader 1000 forms sensing bay 1001 between sensor housings 1011 and 1012. Specimen reader 1000 forms sensing bay 1002 between sensor housings 1012 and 1013. Specimen reader 1000 forms sensing bay 1003 between sensor housings 1013 and 1014. Specimen reader 1000 forms sensing bay 1004 between sensor housings 1014 and 1015. Specimen reader 1000 forms sensing bay 1005 between sensor housings 1015 and 1016.

Specimen reader 1000 further includes a base 1020 from which sensor housings 1011, 1012, 1013, 1014, 1015 and 1016 extend vertically. Base 1020 includes four specimen rack supports 1031, 1032, 1033 and 1034 of which specimen rack supports 1031, 1032, and 1033 are visible in FIG. 10. These specimen rack supports 1031, 1032, 1033 and 1034 mate with and hold specimen rack corners 130G, 130H, 130I and 130J, respectively, in place above base 1020 while a user populates, i.e. inserts specimen holders in, or depopulates, i.e. removes specimen holders from, specimen rack 100. Base 1020 includes an activity indicator light 1025 that lights to indicate a change event and confirm a successful RFID read operation, as described in more detail below.

Base 1020 includes a moisture trough 1035 for collecting water and/or other moisture that may form on specimen rack 100 when refrigeration apparatus stores specimen rack 100. Trough 1035 may extend around the entire perimeter of specimen reader 1000. Trough 1035 collects moisture that may result from the melting of frost on specimen rack 100 when the user removes the specimen rack 100 from refrigeration apparatus and places rack 100 on specimen reader 1000. In this manner, the resultant melted liquid does not reach electronic circuits within base 1020 of specimen reader 1000.

Figure 10B:
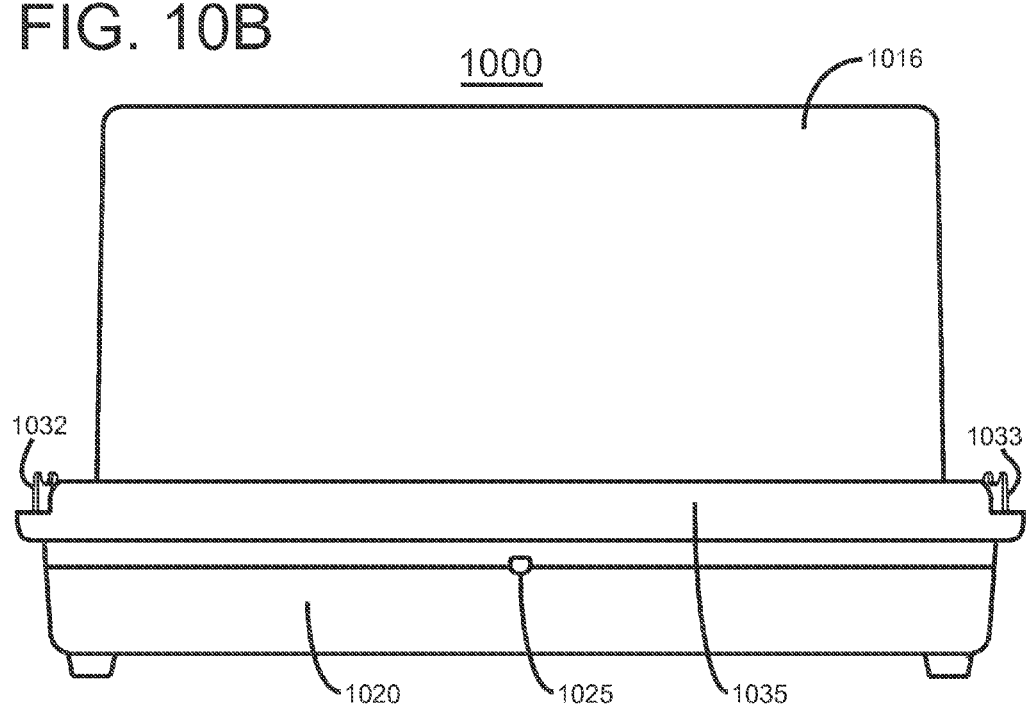
FIG. 10B is a side view of the disclosed specimen reader.
Figure 10C:
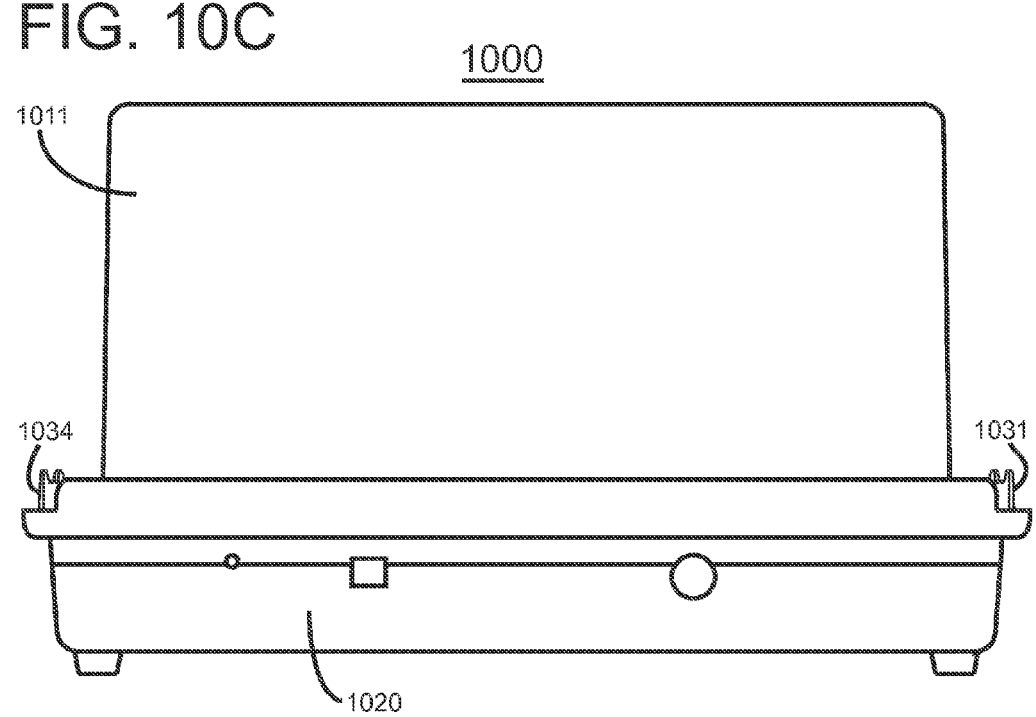
FIG. 10C is a side view of the disclosed specimen reader taken from the side of the specimen reader opposite to that of FIG. 10B

FIG. 10B is a plan view of specimen reader 1000 taken from the side of specimen reader 1000 that includes sensing housing 1016. FIG. 10C is a plan view of specimen reader 1000 taken from the opposed side of specimen reader 1000, namely the side of specimen reader 1000 that includes sensing housing 1011. FIG. 10B shows specimen rack supports 1032 and 1033 as including substantially U-shaped channels that receive respective corners 130H and 130I of specimen rack 100. FIG. 10C shows specimen rack supports 1031 and 1034 as including substantially U-shaped channels that receive the remaining respective corners 130G and 130J of specimen rack 100. In this manner, specimen reader 1000 supports specimen rack 100 atop specimen reader 1000.

Figure 12:
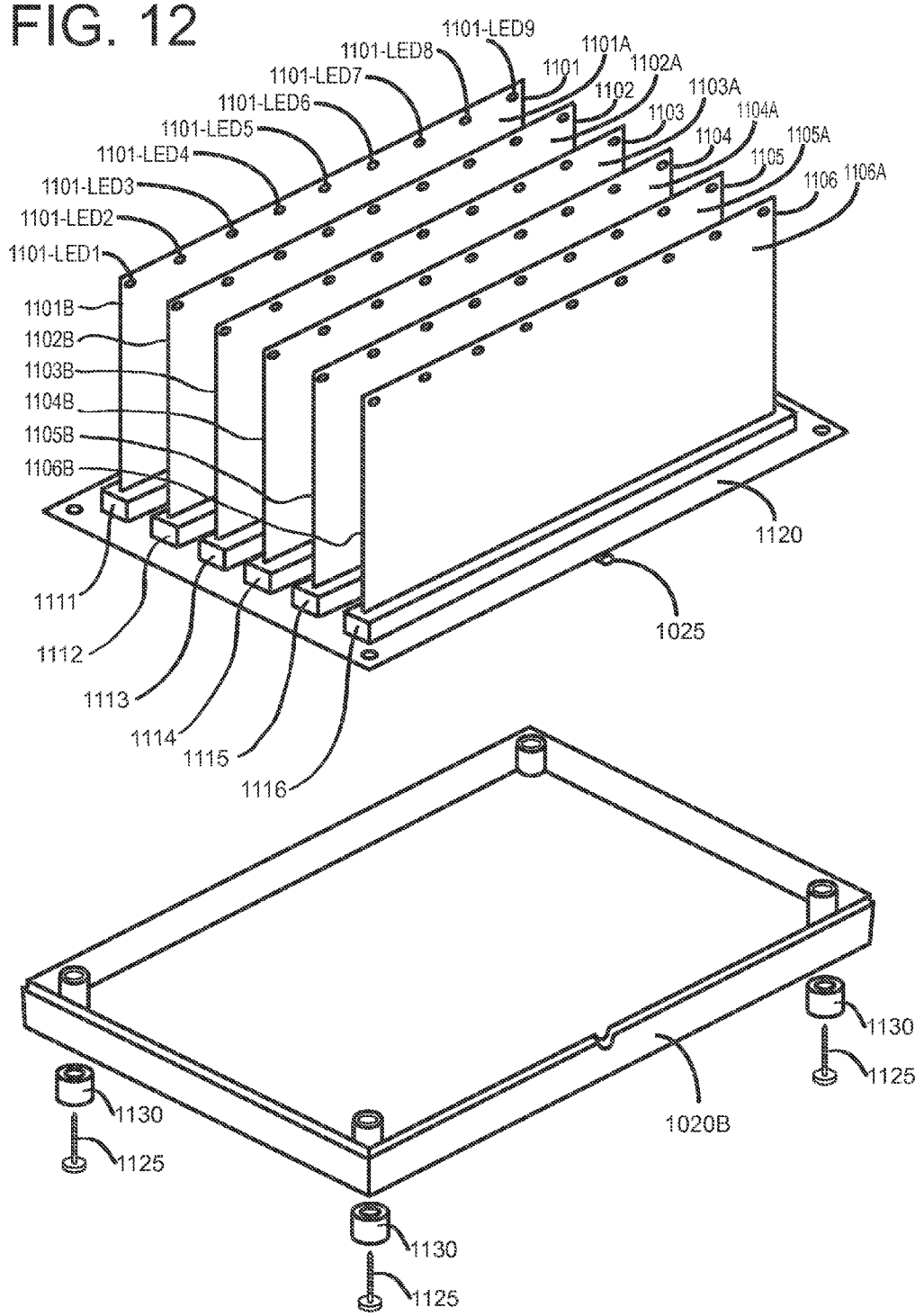
FIG. 12 is a partially exploded perspective view showing the base, motherboard and LED emitter/detector boards of the disclosed specimen reader.

FIG. 11 is an exploded view of specimen reader 1000 including upper base 1020A and lower base 1020B. FIG. 11 separates upper base 1020A from lower base 1020B to reveal six LED emitter/detector boards 1101, 1102, 1103, 1104, 1105 and 1106 that are housed by respective sensor housings 1011, 1012, 1013, 1014, 1015 and 1016. The interior of each of sensor housings 1011, 1012, 1013, 1014, 1015 and 1016 is hollow to receive and house the LED emitter/detector boards 1101, 1102, 1103, 1104, 1105 and 1106, respectively, therein. LED emitter/detector boards 1101, 1102, 1103, 1104, 1105 and 1106 couple via respective connectors 1111, 1112, 1113, 1114, 1115 and 1116 to motherboard 1120. LED emitter/detector boards 1101, 1102, 1103, 1104, 1105 and 1106 include respective sides 1101A, 1102A, 1103A, 1104A, 1105A and 1106A and further include respective opposed sides 1101B, 1102B, 1103B, 1104B, 1105B and 1106B, as shown in FIG. 11 and FIG. 12. FIG. 12 is a partial exploded view of specimen reader 1000 that shows motherboard 1120 and lower base 1020B to provide more detail with respect to these components.

Figure 13A:
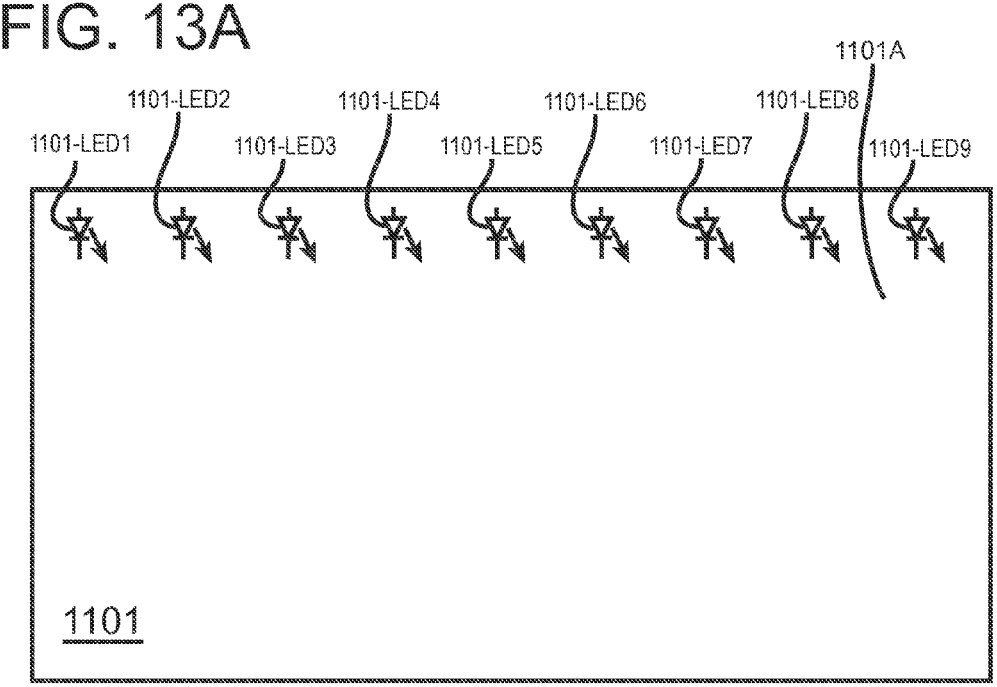
FIG. 13A is a side view of one side of one of the LED emitter/detector boards of the disclosed specimen reader.
Figure 13B:
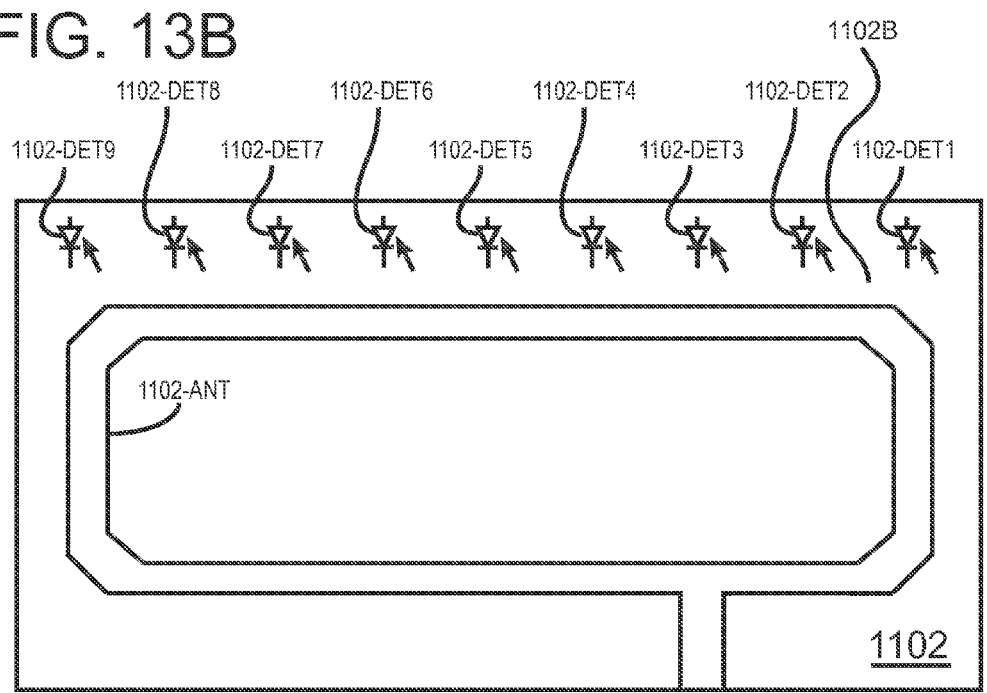
FIG. 13B is a side view of the opposite side of an LED emitter/detector board of the disclosed specimen reader.

In one embodiment, each of LED emitter/detector boards 1101, 1102, 1103, 1104, 1105 and 1106 includes an LED emitter array one one side of the board and an a light detector array on the opposed side of the board. Specimen reader 1000 arranges the LED emitter/detector boards such that each LED emitter of one board faces a corresponding light detector on an adjacent board. Each LED emitter acts as a light transmitter and each light detector acts as a light receiver. Sensor housings 1011, 1012, . . . 1016 include openings (not visible) near the top thereof to allow light from the LEDs to flow therethrough. A transparent cover such as representative cover 1140 covers each of these openings in the sensor housings to form a water seal that allows light to be transmitted into and out of the boards while protecting electronics internal to the sensor housings. FIGS. 13A and 13B together show an arrangement wherein each light generating LED on a particular LED emitter/detector board faces a corresponding light detector on an adjacent LED emitter/detector board.

More particularly, FIG. 13A shows a representative LED emitter/detector board 1101 of which side 1101A includes an array of nine light emitting diodes, 1101-LED1, 1101-LED2, . . . 1101-LED9 mounted thereon. FIG. 13B shows a representative LED emitter/detector board 1102 that is adjacent to LED emitter/detector board 1101. Side 1102B of LED emitter/detector board 1102 faces adjacent side 1101A of LED emitter/detector board 1101 when mounted as shown in FIG. 12. Returning to FIG. 13B, side 1102B of LED emitter/detector board 1102 includes an array of nine photodetectors, 1102-DET1, 1102-DET2, 1102-DET9, namely a respective photodetector for each of the 9 LEDs of board 1101 that face board 1102.

In this manner, there is a one to one correspondence between the LEDs of one emitter/detector board with the photodetectors of an adjacent emitter/detector board. A sensing region, such as sensing region 1401-SR1 of FIGS. 14B, 14C and 14D, is defined between each LED of one board and a corresponding photodetector of an adjacent board. For example, as seen in more detail in FIG. 14C in conjunction with FIGS. 13A and 13B, photodetector 1102-DET1 on emitter/detector board 1102 may receive light from LED 1101-LED1 on adjacent emitter/detector board 1101, provided no specimen holder is in the sensing region 1401-SR1 between photodetector 1102-DET1 and LED 1101-LED1. If a specimen holder is in the sensing region 1401-SR1 between photodetector 1102-DET1 and LED 1101-LED1, the specimen holder will block the light transmitted by LED 1101-LED1 from reaching photodetector 1102-DET1. The detection of this light blockage signifies the presence of a specimen holder at the sensing region 1401-SR1 between LED 1101-LED1 and photodetector 1102-DET1, in this representative example. In one embodiment, each sensing region of reader 1000 corresponds to a respective specimen holder receiving slot of specimen rack 100, when the user positions rack 100 on reader 1000. In other words, when the user places specimen rack 100 on specimen reader 1000, each specimen holder receiving slot extends into a respective sensing region of specimen reader 1000.

In one embodiment, each of LED emitter/detector boards 1101-1106 includes an antenna that transmits a radio frequency signal to those specimen holders in specimen rack 100 that are in range of the antenna. While in the particular embodiment shown, each of boards 1101-1106 may include an antenna such as antenna 1102-ANT of board 1102 of FIG. 13B, all of these antennas need not be active at a particular point in time.

Figure 14A:
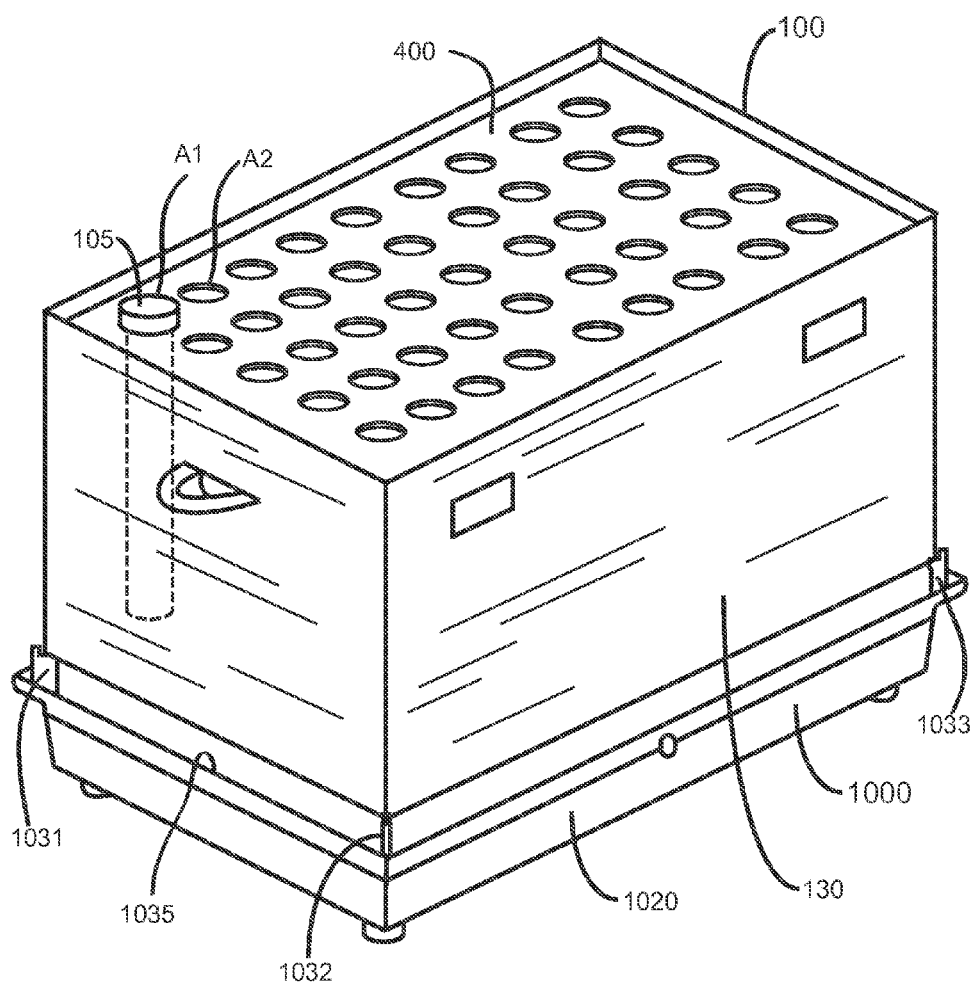
FIG. 14A is a perspective view of the disclosed specimen rack sitting on the disclosed specimen reader.
Figure 14B:
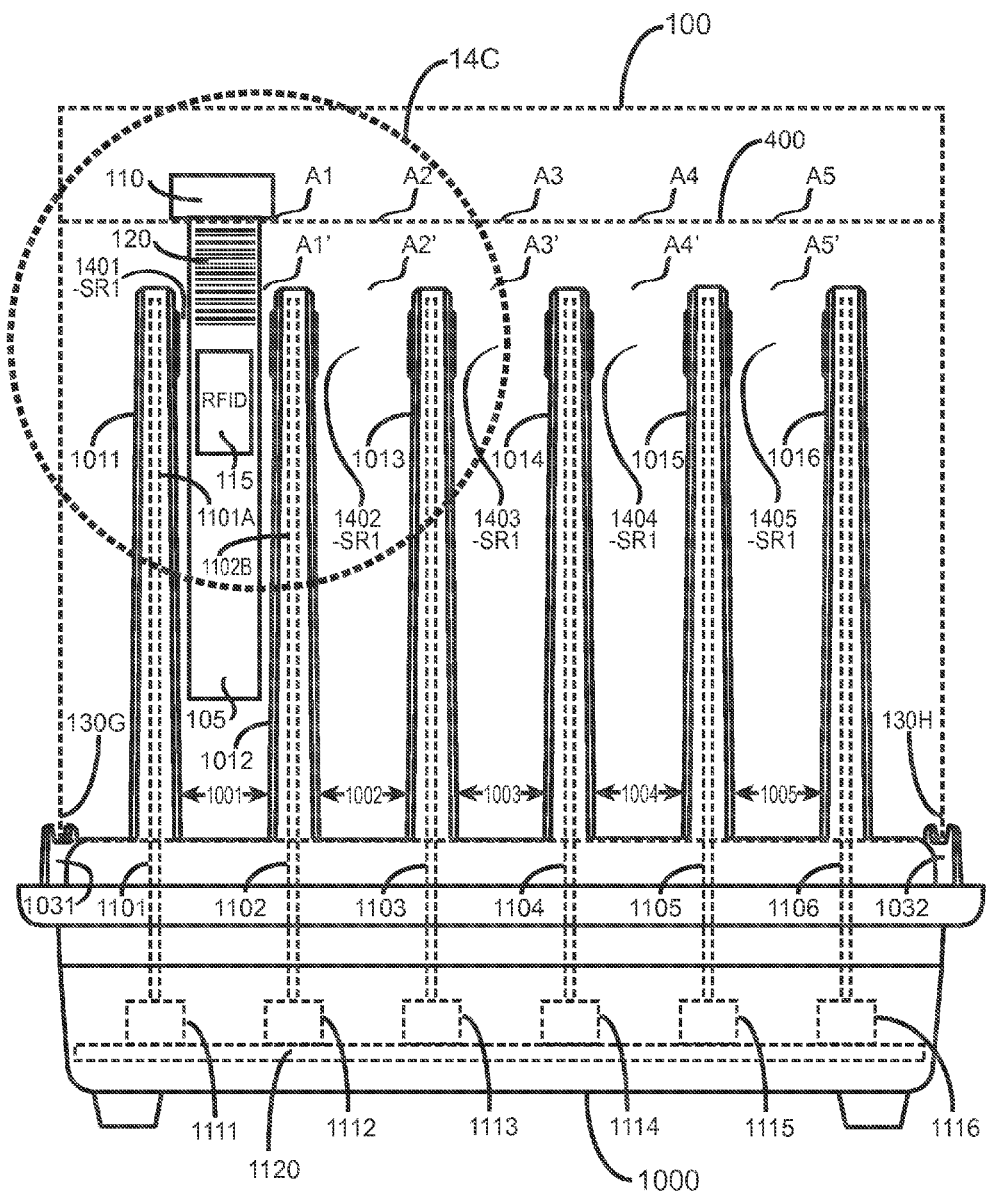
FIG. 14B is an end view of the disclosed specimen reader showing a specimen holder in the specimen rack.
Figure 14C:
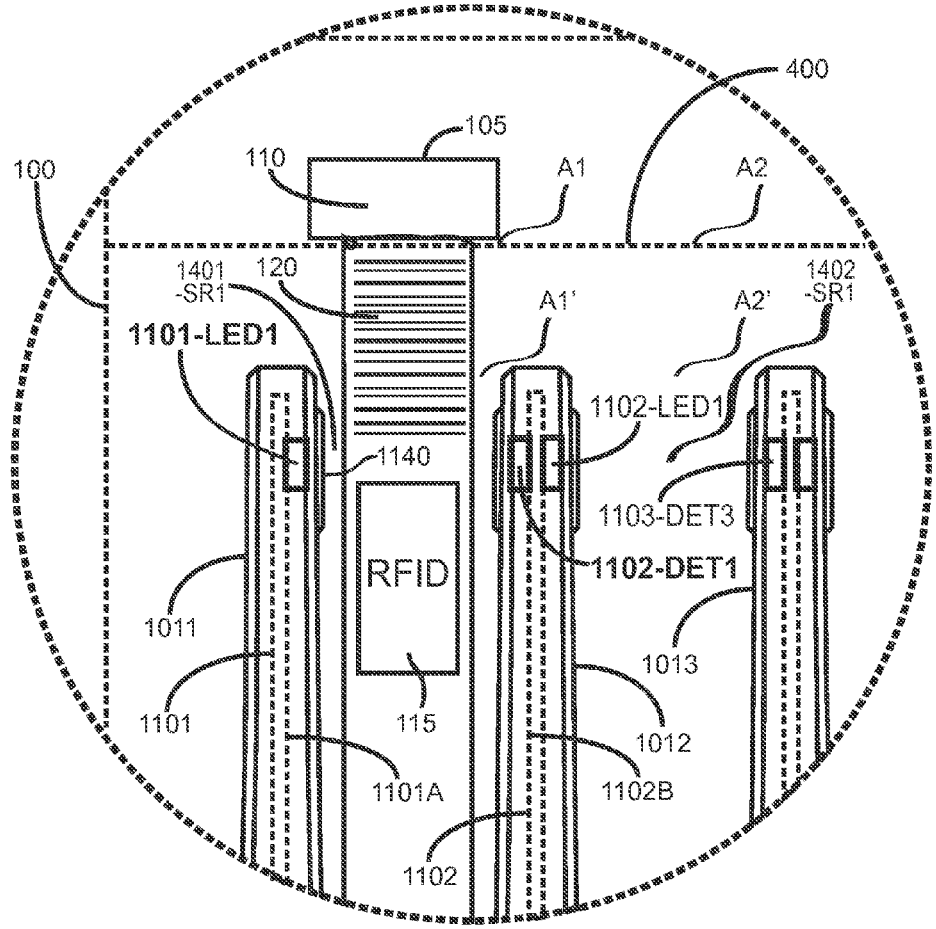
FIG. 14C is a close-up view of a portion of FIG. 14B that is enlarged to make the LEDs and photodetectors more visible in a representative sensing bay.
Figure 14D:
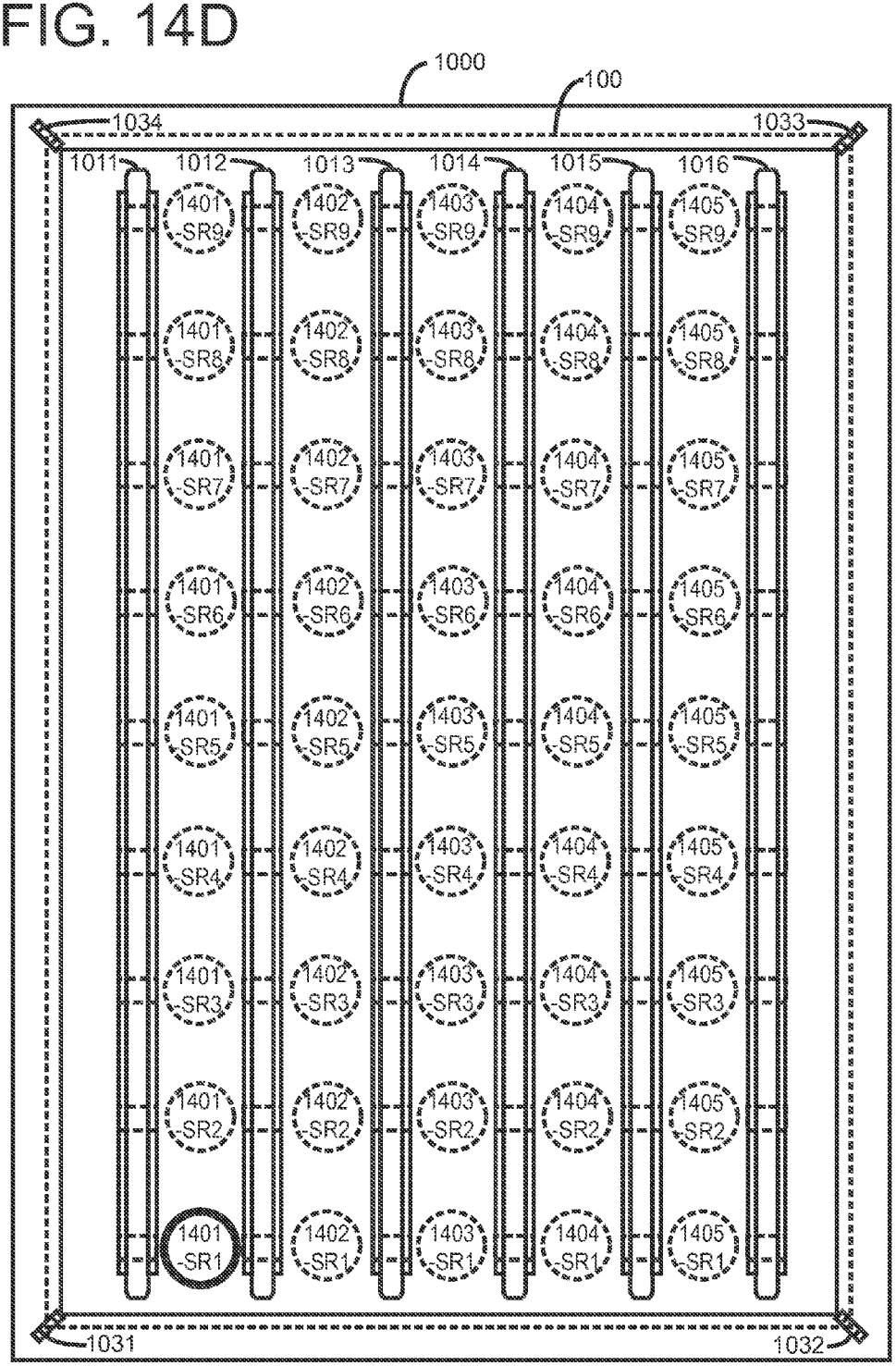
FIG. 14D is a top view of the disclosed specimen reader.

FIG. 14A shows specimen reader 1000 with specimen rack 100 situated thereon. Once the user places specimen rack 100 on specimen reader 1000, specimen rack 100 is ready for populating with specimen holders. For example, after placing specimen rack 100 on specimen reader 1000, the user places a specimen holder 105 (with specimen inside) in slot A1 of specimen rack 100. After placing specimen holder 104 in slot A1 in this manner, the specimen holder 105 extends into the specimen holder receiving region below opening A1, as indicated in dashed line in FIG. 14A. Although FIG. 14A shows slot A1 as being the first slot that the user populates, the user may begin populating specimen rack 100 at any one of the slots in removable insert 400 of specimen rack 100.

When the user places specimen rack 100 on specimen reader 1000 in the manner described above, each slot of specimen rack 100 aligns with a corresponding sensing region of specimen reader 1000. For example, FIG. 14B is a view of specimen rack 100 and specimen reader 1000 which shows that specimen holder receiving region A1' of slot A1 of specimen rack 100 aligns with sensing region 1401-SR1 of specimen reader 1000. In one embodiment, at least a portion of each specimen holder receiving region of rack 100 is coextensive with, i.e. overlaps, a respective sensing region of reader 1000. FIG. 14B shows specimen rack 100 including removable support member 400 in dashed lines. Specimen rack 100 includes corners 130G and 130H that respectively rest in the U-shaped channels of specimen rack supports 1031 and 1032.

FIG. 14C shows an enlarged detail of a portion of FIG. 14B to provide more clarity with respect to the spatial relationship of a representative light emitting diode 1101-LED1 and a corresponding photodetector 1102-DET1. Light emitting diode 1101-LED1 and photodetector 1102-DET1 together form an LED-photodetector pair. Light emitting diode 1101-LED1 is situated on board 1101 and photodetector 1102-DET1 is situated on adjacent board 1102, as shown in FIG. 14C. This arrangement forms a sensing region 1401-SR1 between light emitting diode 1101-LED1 on board 1101 and photodetector 1102-DET1 on board 1102. When there is no specimen holder in sensing region 1401-SR1, light from light emitting diode 1101-LED1 flows freely to photodetector 1102-DET1 and is detected thereby. In other words, detection of light by photodetector 1102-DET1 indicates that there is no specimen holder in sensing region 1401-SR1. The variable "LIGHT" describes the current state of light detection by photodetector 1102-DET1. When photodetector 1102-DET1 detects light from light emitting diode 1101-LED1, then LIGHT=1. This indicates that there is no specimen holder in sensing region 1401-SR1. However, when a user places specimen holder 105 in sensing region 1401-SR1, the specimen holder blocks transmission of light from light emitting diode 1101-LED1 to photodetector 1102-DET1. Under these conditions no light reaches photodetector 1102-DET1 and thus LIGHT=0. This indicates that a specimen holder is now present in sensing region 1401-SR1. This change from "LIGHT=1 to LIGHT=0 is a change event, namely an insertion change event. In contrast, a change from "LIGHT=0" to "LIGHT=1" indicates a removal change event.

The user populates specimen rack 100 on specimen reader 1000 with specimen holders one at a time. Specimen reader 1000 periodically scans all LED-photodetector pairs to determine if a change event occurred for any particular LED-photodetector pair in the reader. To determine if a change event occurred, for each sensing region, specimen reader 1000 compares the value of LIGHT in the current scan of all LED-photodetector pairs with the value of LIGHT in an immediately prior scan of all LED-photodetector pairs. If for any sensing region the value LIGHT changes from LIGHT=1 to LIGHT=0, this indicates an insertion change event. However, if for any sensing region the value LIGHT changes from LIGHT=0 to LIGHT=1, this indicates an removal change event. Reader 1000 stores the current and prior value of LIGHT in a database, as described in more detail below. In one embodiment, the user commences population of specimen rack 100 or specimen reader 1000 by placing an empty specimen rack 100 on specimen reader 1000. Specimen reader 1000 will thus detect a value LIGHT=1 for all sensing regions of reader 1000 and all corresponding slots of specimen rack 100. This indicates that light is detected for all sensing regions and that there are thus no specimen holders present in any sensing regions.

FIG. 14D shows a simplified top view of specimen rack 100 on specimen reader 1000. The periphery of specimen rack 100 and removable insert member 400 are shown in dashed line to more clearly show the structures of specimen reared 1000 below specimen rack 100. Specimen reader 1000 includes rows of sensing regions, namely a row 1401-SR1, 1401-SR2, . . . 1401-SR9, a row 1402-SR1, 1402-SR2, . . . 1402-SR9, a row 1403-SR1, 1403-SR2, . . . 1403-SR9, a row 1404-SR1, 1404-SR2, . . . 1404-SR9 and a row 1405-SR1, 1405-SR2, . . . 1405-SR9. These sensing regions are shown as dashed circles, except for sensing region 1401-SR1 which is shown in solid bold line to indicate that the user placed a specimen holder in a specimen holder receiving slot that corresponds to sensing region 1401-SR1.

FIG. 15 shows a simplified block diagram of specimen reader 1000. Although for clarity FIG. 15 shows motherboard 1120 and several of its components separated from the LED emitter/detector boards 1101, 1102, 1103, 1104, 1105 and 110, in actual practice motherboard 1120 may be situated below these boards. FIG. 14B shows this arrangement. Returning to FIG. 15, motherboard 1120 includes a processor 1505 such as a microcontroller that controls the sensing of specimen holders when a user places a specimen rack 100 on specimen reader 1000. Processor 1505 includes a memory 1510 that stores microcode that governs the operation of specimen reader 1000. In one embodiment, memory 1510 is nonvolatile memory. Processor 1505 may couple to an external host 1515 that includes volatile and/or nonvolatile storage shown generally as memory 1520. Host 1515 is an information handling system (IHS) that may couple specimen reader 1000 to other IHSs (not shown) via a network 1513. In this manner, specimen reader 1000 may supply such other IHSs with an inventory of the specimens in any particular specimen rack 100 that specimen reader 1000 scans and interrogates.

In the particular embodiment shown, specimen reader 1000 includes five (5) rows of sensing regions, each row including nine (9) sensing regions. Those skilled in the art will appreciate that the disclosed methodology is readily adaptable to accommodate a greater or lesser number of rows and/or a greater or lesser number of sensing regions per row. By way of example, sensing regions 1401-SR1 and 1401-SR9 are sensing regions at the opposed ends of one row of specimen reader 1000. Sensing regions 1405-SR1 and 1405-SR9 are sensing regions at the opposed ends of another row of specimen reader 1000.

Figure 16A:
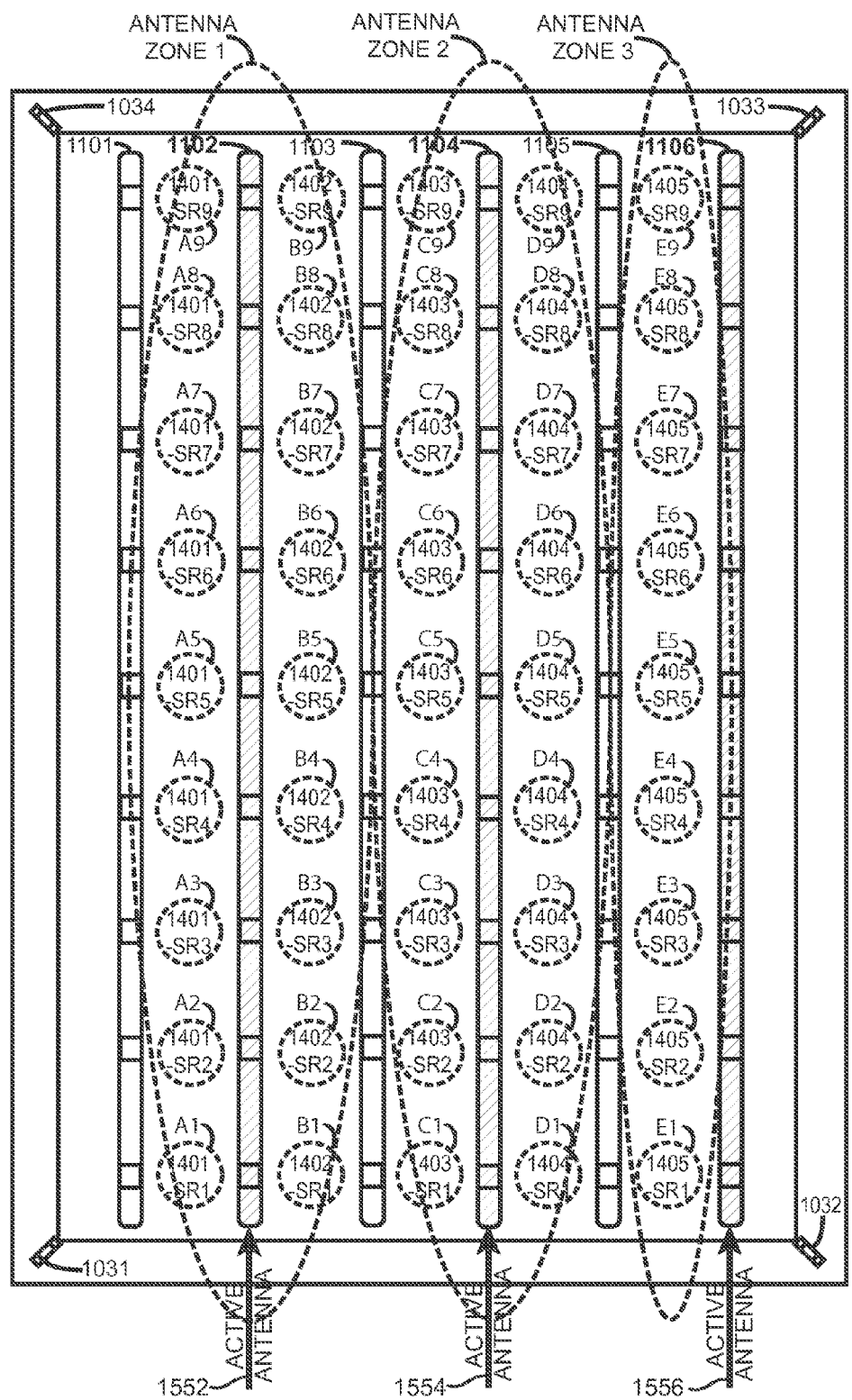
FIG. 16A is a top view of the disclosed specimen reader prior to populating the specimen rack with specimen holders.

Specimen reader 1000 may use a processor such as the MSP430 available from Texas Instruments as processor 1505 to control the optical scanning of the sensing regions for change events. Processor 1505 may also control the reading of RFIDs of specimen holders within specimen rack 100 on specimen reader 1000. While each LED emitter/detector board may include a respective RFID loop antenna such as antenna 1102-ANT of board 1102 of FIG. 13B, in one embodiment it is not necessary to excite all of these antennas to interrogate the RFIDs of the specimen holders in specimen rack 100 on specimen reader 1000. For example, in the embodiment that FIG. 15 depicts, processor 1505 interrogates, i.e. excites with an RF interrogation signal, the antennas of alternating boards of specimen reader 1000, namely the antennas of boards 1102, 1104 and 1106, at different times. The antennas of boards 1102, 1104 and 1106 are thus active antennas as noted in FIG. 16A, whereas the remaining antennas of boards 1101, 1103 and 1105 are inactive in this embodiment. FIG. 16A shows a representation of specimen reader 1000 prior to inserting specimen holders in the specimen rack 100 (not shown) that sits on top of specimen reader 1000. While FIG. 16A does not specifically show specimen rack 100, FIG. 16A does show the positions of the specimen holder receiving slots A1-A9, B1-B9, C1-C9, D1-D9 and E1-E9 in specimen rack 100 relative to the positions of respective sensing regions 1401-SR1 . . . 1401-SR9, 1402-SR1 . . . 1402-SR9, 1403-SR1 . . . 1403-SR9, 1404-SR1 . . . 1404-SR9, and 1405-SR1 . . . 1405-SR9 of specimen reader 1000. There is a one to one correspondence between the location of the specimen holder receiving slots of rack 100 and the sensing regions of reader 1000, each slot of rack 100 extending into a respective sensing region of reader 1000.

Returning to FIG. 15, to excite the antennas of boards 1102, 1104 and 1106 with an RF interrogation signal at different times, processor 1505 employs respective RFID readers 1522, 1524 and 1526. Each RFID reader includes both an RF transmitter that transmits RFID interrogation signals and an RF receiver that receives RFID response signals. One RFID reader that is suitable for RFID readers 1522, 1524 and 1526 is the Model TRF7960 RFID reader by Texas Instruments. Control/data busses 1532, 1534 and 1536 couple processor 1505 to RFID readers 1522, 1524 and 1526. Upon instruction by processor 1505, RFID readers 1522, 1524 and 1526 transmit RF excitation signals, i.e. interrogation signals, at their respective TX outputs and receive responsive RFID signals from any excited RFID tags on their respective RX inputs. Impedance matching (Z match) circuits 1542, 1544 and 1546 couple the TX outputs and RX inputs of RFID readers 1522, 1524 and 1526 to respective boards 1102, 1104 and 1106 via antenna transmission lines 1552, 1554 and 1556 as shown in FIG. 15. Antenna transmission lines 1552, 1554 and 1556 may be coaxial cable or microstrip transmission lines.

In this particular embodiment, the configuration of the antennas on active boards 1102, 1104, 1106 and the RF power levels selected to drive these antennas, are such that the resultant RFID interrogation signals are sufficiently strong to excite the RFID tags of specimen holders in the two rows adjacent to an active board. For example, the antenna on active board 1102 may generate an RF interrogation signal of sufficient strength that interrogates those sensing regions one row either side of active board 1102, namely antenna zone 1, as shown in FIG. 16A. Antenna zone 1 includes sensing regions 1401-SR1 to 1401-SR9 and sensing regions 1402-SR1 to 1402-SR9. The antenna on active board 1104 may generate an RF interrogation signal of sufficient strength to interrogate those sensing regions one row either side of active board 1104, namely antenna zone 2. Antenna zone 2 includes sensing regions 1403-SR1 to 1403-SR9 and sensing regions 1404-SR1 to 1404-SR9. The antenna on active board 1106 may generate an RF interrogation signal of sufficient strength to interrogate those sensing regions one row either side of active board 1106, namely antenna zone 3. Antenna zone 3 is drawn as including only sensing regions 1405-SR1 to 1404-SR5 because active board 1106 is at the end of specimen reader where there is no sensing bay external to the specimen reader.

Processor 1505 may turn on the respective antennas on active boards in antenna zones 1, 2 and 3 at different times to collect responsive RFIDs from the specimen holders in those zones. Processor 1505 interrogates those specimen holders in a particular antenna zone by instructing an RFID reader to transmit an interrogation signal to that particular antenna zone. In response, the RFID tags on any specimen holders currently in the sensing regions within that particular antenna zone transmit RFID response signals. The RFID response signal from a particular RFID tag may include a unique identifier for that particular RFID tag as well as other data.

More particularly, to interrogate those specimen holders in a sensing region within antenna zone 1, processor 1505 sends an appropriate control signal to RFID reader 1522 on bus 1532. In response, RFID reader 1522 sends an RF interrogation signal via its TX output to impedance matching circuit 1542. Impedance matching circuit 1542 matches the output impedance of the TX output of RFID reader 1522 to the antenna of active board 1102. When the RF interrogation signal radiates to specimen holders within the sensing regions of antenna zone 1, in response the RFID tags of those specimen holders transmit their respective RFID response signals back to processor 1505 via impedance matching circuit 1542, the receiver (RX) input of RFID reader 1522 and control/data bus 1532. In actual practice, RFID reader 1522 demodulates the RFID response signal to provide the RFID tag's unique identifier and data to processor 1505. Processor 1505 stores the received RFIDs, i.e. the RFID unique identifiers, from those specimen holders in zone 1 in a local database 1511 that resides in nonvolatile storage 1512 internal to, or external to, processor 1505. The term RFID, or RFID response signal, is used to indicate the unique identifier of a particular RFID tag and other data resident in the tag. Processor 1505 may alternatively, or additionally, store the received RFIDs from antenna zone 1 in a master database 1516 in nonvolatile storage 1517 internal or external to processor 1505 and/or in other storage such as volatile and/or nonvolatile memory 1520 in host IHS 1515. In one embodiment, master database 1516 may store the same content as database 1511.

In a similar manner, to interrogate those specimen holders in a sensing region within antenna zone 2, processor 1505 sends an appropriate control signal to RFID reader 1524 on bus 1534. In response, RFID reader 1524 sends an RF interrogation signal via its TX output to impedance matching circuit 1544. Impedance matching circuit 1544 matches the output impedance of the TX output of RFID reader 1524 to the antenna of active board 1104. When the RF interrogation signal radiates to specimen holders within the sensing regions of antenna zone 2, in response the RFID tags of those specimen holders transmit their respective RFID response signals back to processor 1505 via impedance matching circuit 1544, the receiver (RX) input of RFID reader 1524 and control/data bus 1534. Processor 1505 stores the received RFIDs, including unique identifiers and data, from those specimen holders in zone 2 in the database 1511 that resides in nonvolatile storage 1512. Processor 1505 may alternatively, or additionally, store the received RFIDs from antenna zone 2 in the master database 1516 in nonvolatile storage 1517 that couples to host 1515.

Likewise, to interrogate those specimen holders in a sensing region within antenna zone 3, processor 1505 sends an appropriate control signal to RFID reader 1526 on bus 1536. In response, RFID reader 1526 sends an RF interrogation signal via its TX output to impedance matching circuit 1546. Impedance matching circuit 1546 matches the output impedance of the TX output of RFID reader 1526 to the antenna of active board 1106. When the RF interrogation signal radiates to specimen holders within the sensing regions of antenna zone 3, in response the RFID tags of those specimen holders transmit their respective RFID response signals, including unique identifiers and data, back to processor 1505 via impedance matching circuit 1546, the receiver (RX) input of RFID reader 1526 and control/data bus 1536. Processor 1505 stores the received RFIDs, including unique identifiers and data, from those specimen holders in zone 3 in the database 1511 that resides in nonvolatile storage 1512. Processor 1505 may alternatively, or additionally, store the received RFIDs from antenna zone 3 in the database 1516 in nonvolatile storage 1517 that couples to host 1515.

In the above described manner, processor 1505 may determine the RFIDs, i.e. the unique identifiers, of any specimen holder in antenna zones 1, 2 and 3. However, in a preferred embodiment, processor 1505 optically scans the 45 sensing regions of specimen reader 1000 to determine a change event before sending RFID interrogation signals to the 3 antenna zones to determine an RFID associated with the change event. As noted above, specimen reader 1000 includes 45 sensing regions, such as sensing region 1401-SR1, that each employ a light emitting diode such as 1101-LED1 and an associated photodetector such as 1102-DET1 to optically detect the presence of a specimen holder in a sensing region between the LED and the photodetector. Each of the sensing regions employs 2 input output (I/O) lines, namely an I/O line to drive the LED and an I/O line to transmit the photodetector state back to processor 1505. FIG. 15 represents these 90 I/O lines collectively as optical sense bus 1590. The hash mark designated "90" adjacent the oval that encompasses optical sense bus 1590 signifies that bus 1590 includes 90 I/O lines in this embodiment. A multiplexer 1560 couples an I/O port of processor 1505 to I/O optical sense bus 1590. Multiplexer 1560 enables processor 1505 to optically scan each of the 45 sensing regions to determine if a specimen holder is present therein.

In preparation for the first scan of a specimen rack 100, the user turns specimen reader 1000 on. The user places an empty specimen rack 100 on specimen reader 1000 in the position shown in FIG. 14A. No specimens are in the specimen rack 100 at this time. In this state, at time T=T0, an optical scan of the 45 sensing regions will show no specimen holders are present in any of the sensing regions, and a radio frequency (RF) scan for RFIDs will show no RFID tags present in specimen rack 100, except for the RFID tag 125 on specimen rack 100 itself. Under these conditions, processor 1505 initializes database 1511 to the initial configuration that TABLE 1 shows below:

TABLE 1

LOCAL DATABASE
TIME T = T0 (no Specimen Holders in Rack)

| 1401-SR9/A9 | 1402-SR9/B9 | 1403-SR9/C9 | 1404-SR9/D9 | 1405-SR9/E9 |
|---|---|---|---|---|
| LIGHT = 1 | LIGHT = 1 | LIGHT = 1 | LIGHT = 1 | LIGHT = 1 |
| RFID = 0 | RFID = 0 | RFID = 0 | RFID = 0 | RFID = 0 |
| BARCODE = 0 | BARCODE = 0 | BARCODE = 0 | BARCODE = 0 | BARCODE = 0 |
| ANT ZONE = 1 | ANT ZONE = 1 | ANT ZONE = 2 | ANT ZONE = 2 | ANT ZONE = 3 |
| . | . | . | . | . |
| . | . | . | . | . |
| . | . | . | . | . |
| 1401-SR3/A3 | 1402-SR3/B3 | 1403-SR3/C3 | 1404-SR3/D3 | 1405-SR3/E3 |
| LIGHT = 1 | LIGHT = 1 | LIGHT = 1 | LIGHT = 1 | LIGHT = 1 |
| RFID = 0 | RFID = 0 | RFID = 0 | RFID = 0 | RFID = 0 |
| BARCODE = 0 | BARCODE = 0 | BARCODE = 0 | BARCODE = 0 | BARCODE = 0 |
| ANT ZONE = 1 | ANT ZONE = 1 | ANT ZONE = 2 | ANT ZONE = 2 | ANT ZONE = 3 |
| 1401-SR2/A2 | 1402-SR2/B2 | 1403-SR2/C2 | 1404-SR2/D2 | 1405-SR2/E2 |
| LIGHT = 1 | LIGHT = 1 | LIGHT = 1 | LIGHT = 1 | LIGHT = 1 |
| RFID = 0 | RFID = 0 | RFID = 0 | RFID = 0 | RFID = 0 |
| BARCODE = 0 | BARCODE = 0 | BARCODE = 0 | BARCODE = 0 | BARCODE = 0 |
| ANT ZONE = 1 | ANT ZONE = 1 | ANT ZONE = 2 | ANT ZONE = 2 | ANT ZONE = 3 |
| 1401-SR1/A1 | 1402-SR1/B1 | 1403-SR1/C1 | 1404-SR1/D1 | 1405-SR1/E1 |
| LIGHT = 1 | LIGHT = 1 | LIGHT = 1 | LIGHT = 1 | LIGHT = 1 |
| RFID = 0 | RFID = 0 | RFID = 0 | RFID = 0 | RFID = 0 |
| BARCODE = 0 | BARCODE = 0 | BARCODE = 0 | BARCODE = 0 | BARCODE = 0 |
| ANT ZONE = 1 | ANT ZONE = 1 | ANT ZONE = 2 | ANT ZONE = 2 | ANT ZONE = 3 |

In this particular example, the rows and columns of the local database 1511 correspond to the configuration of the sensing regions 1401-SR1, 1401-SR2, . . . 1405-SR9 of specimen reader 1000. Each specimen holder receiving slot of specimen rack 100 corresponds to a respective, like-positioned sensing region of specimen reader 1000. FIG. 16A visually depicts spacemen reader 1000 with no sensing regions occupied by a specimen holder in specimen rack 100 on reader 1000. All sensing regions are empty prior to population of specimen rack 100. Table 1 shows local database 1511 as it exists prior to the user populating specimen rack 100 with specimen holders, i.e. when the specimen rack is empty, as FIG. 16A shows. In other words, the local database 1511 of Table 1 represents the empty sensing regions and corresponding rack slots of the empty specimen rack 100 that FIG. 16A depicts.

For purposes of example, a representative sensing region, 1401-SR1 is now discussed. Sensing region 1401-SR1 of specimen reader 1000 corresponds to slot A9 of specimen rack 100. The database entry for sensing region 1401-SR1 (slot A1) includes an entry for the variable LIGHT that indicates whether or not processor 1505 found that there is a specimen holder in sensing region 1401-SR1. To perform this determination, processor 1505 instructs multiplexer 1560 to turn on the LED corresponding to sensing region 1401-SR1 and to receive a LIGHT value from the corresponding photodetector. Since in this example there is no specimen holder in sensing region 1401-SR1, the light beam from the LED will reach the photodetector. In response, the photodetector sends a logic value, LIGHT=1, back to processor 1505 to indicate the photodetector detects light and that a specimen holder is not present in sensing region 1401-SR1. In other words, LIGHT=1 means that a specimen is not present in this sensing region. However, if the light beam is broken by a specimen holder in the sensing region, then light does not reach the photodetector and LIGHT=0. Thus, LIGHT=0 would indicate the presence of a specimen holder at the sensing region. However, for time T=T0, wherein the specimen rack contains no inserted specimen holders, the database entry for sensing region 1401-SR1 indicates LIGHT=1, as seen in TABLE 1 above.

Continuing with the discussion of TABLE 1, wherein no specimen holders are in specimen rack 100, processor 1505 will detect no RFIDs in the three (3) antenna zones of specimen reader 1000. Thus, there will be no RFID associated with representative sensing region 1401-SR1. Detecting no RFID means that no unique identifier code or data is detected from an RFID tag. For this reason, the database entry for sensing region 1401-SR1 will include a value RFID=0 to indicate that specimen reader 1000 currently associates no RFID with this sensing region 1401-SR1. Before the first optical scan for specimen holders and the first RF scan for RFIDs of specimen holders, processor 1505 may initialize the entry for sensing region 1401-SR1 with a value of RFID=0 to indicate the lack of an RFID associated with that particular sensing region. Processor 1505 may initialize the RFID values of all of the other sensing region entries in the database 1511 to likewise indicate that no RFID is currently associated with those sensing regions (i.e. RFID=0).

In an embodiment wherein specimen reader 1000 includes multiple antenna zones, such as the three (3) antenna zones that FIG. 16A depicts, database 1511 initializes to fixed antenna zone values (ANT ZONE) as shown in TABLE 1. For example, sensing regions 1401-SR1 . . . 1401-SR9 and 1402-SR1 . . . 1402-SR9 within antenna zone 1 exhibit ANT ZONE=1. Sensing regions 1403-SR1 . . . 1403-SR9 and 1404-SR1 . . . 1404-SR9 within antenna zone 2 exhibit ANT ZONE=2. Sensing regions 1405-SR1 . . . 1405-SR9 within antenna zone 3 exhibit ANT ZONE=3. In one embodiment, these antenna zone values are fixed and do not change during operation of specimen reader 1000.

FIG. 16A shows sensing region 1401-SR1 with a dashed circle to indicate that there is initially no specimen holder in sensing region 1401-SR1. Dashed circles are used throughout FIGS. 15 and 16A-16D to indicate those sensing regions that do not contain a specimen holder. In contrast, bold solid circles indicate that a particular sensing region currently contains a specimen holder. At a time T=T1 after initialization of the local database 1511 to the values shown in TABLE 1 above, the user places a specimen holder in sensing region 1401-SR1 of specimen reader 100. When the user places the specimen holder in slot A1 of specimen rack 100, this action inserts the specimen holder into sensing region 1401-SR1 because sensing region 1401-SR1 of specimen reader 1000 positionally corresponds to slot A1 of specimen rack 100. More specifically, when the user inserts a specimen holder into specimen rack 100 in this manner, this actually places the specimen holder in the region between light emitting diode 1101-LED1 of board 1101 and photodetector 1102-DET1 of board 1102, namely sensing region 1401-SR1, as seen in FIG. 14B and in more detail in FIG. 14C.

When processor 1505 instructs the optical scan of the 45 sensing regions of antennas zones 1, 2 and 3, processor 1505 will detect the presence of the specimen holder at sensing region 1401-SR1. Processor 1505 performs this optical scan by activating each of the 45 LEDs of specimen reader 1000 and monitoring the respective outputs of 45 corresponding photodetectors to see if the respective light beams are blocked. If a specimen holder blocks the light beam, then the value of LIGHT transitions from its initial value of LIGHT=1 to a current value of LIGHT=0. Processor 1505 updates database 1511 accordingly to indicate that the current database entry for sensing region 1401-SR1 now includes an associated entry LIGHT=0, thus denoting the presence of a specimen holder inserted in sensing region 1401-SR1, as shown in TABLE 2 below.

TABLE 2

| LOCAL DATABASE TIME T = T1 (Insertion Change Event) | | | | |
|---|---|---|---|---|
| 1401-SR9/A9 | 1402-SR9/B9 | 1403-SR9/C9 | 1404-SR9/D9 | 1405-SR9/E9 |
| LIGHT = 1 | LIGHT = 1 | LIGHT = 1 | LIGHT = 1 | LIGHT = 1 |
| RFID = 0 | RFID = 0 | RFID = 0 | RFID = 0 | RFID = 0 |

TABLE 2-continued

LOCAL DATABASE
TIME T = T1 (Insertion Change Event)

| BARCODE = 0 | ANT ZONE = 1 | ANT ZONE = 2 | ANT ZONE = 2 | ANT ZONE = 3 |
| ANT ZONE = 1 | BARCODE = 0 | BARCODE = 0 | BARCODE = 0 | BARCODE = 0 |
| . | . | . | . | . |
| . | . | . | . | . |
| . | . | . | . | . |
| 1401-SR3/A3 | 1402-SR3/B3 | 1403-SR3/C3 | 1404-SR3/D3 | 1405-SR3/E3 |
| LIGHT = 1 | LIGHT = 1 | LIGHT = 1 | LIGHT = 1 | LIGHT = 1 |
| RFID = 0 | RFID = 0 | RFID = 0 | RFID = 0 | RFID = 0 |
| BARCODE = 0 | BARCODE = 0 | BARCODE = 0 | BARCODE = 0 | BARCODE = 0 |
| ANT ZONE = 1 | ANT ZONE = 1 | ANT ZONE = 2 | ANT ZONE = 2 | ANT ZONE = 3 |
| 1401-SR2/A2 | 1402-SR2/B2 | 1403-SR2/C2 | 1404-SR2/D2 | 1405-SR2/E2 |
| LIGHT = 1 | LIGHT = 1 | LIGHT = 1 | LIGHT = 1 | LIGHT = 1 |
| RFID = 0 | RFID = 0 | RFID = 0 | RFID = 0 | RFID = 0 |
| BARCODE = 0 | BARCODE = 0 | BARCODE = 0 | BARCODE = 0 | BARCODE = 0 |
| ANT ZONE = 1 | ANT ZONE = 1 | ANT ZONE = 2 | ANT ZONE = 2 | ANT ZONE = 3 |
| 1401-SR1/A1 | 1402-SR1/B1 | 1403-SR1/C1 | 1404-SR1/D1 | 1405-SR1/E1 |
| LIGHT = 0 | LIGHT = 1 | LIGHT = 1 | LIGHT = 1 | LIGHT = 1 |
| RFID = 10001001 | RFID = 0 | RFID = 0 | RFID = 0 | RFID = 0 |
| BARCODE = 411 121 | BARCODE = 0 | BARCODE = 0 | BARCODE = 0 | BARCODE = 0 |
| ANT ZONE = 1 | ANT ZONE = 1 | ANT ZONE = 2 | ANT ZONE = 2 | ANT ZONE = 3 |

In one embodiment of the specimen reader, the user inserts specimen holders one at a time in the rack on the reader. Processor 1505 continually optically scans the 45 specimen regions, repeating the complete optical scan over and over when the user activates specimen reader 1000. With each complete scan of the 45 specimen regions, processor 1505 determines if the LIGHT value of any particular specimen region changed from the immediately prior scan. Processor 1505 may access database 1511 to make this determination. Processor 1505 performs this determination by comparing the current LIGHT value of each specimen region from the current scan with the corresponding LIGHT value of that specimen region in the immediately prior scan.

If the LIGHT value of any particular sensing region changes from LIGHT=1 (beam detected) in the immediately prior scan to a current LIGHT value of LIGHT=0 (beam blocked), this indicates that the user inserted a specimen holder into that particular sensing region after the prior complete optical scan. However, if the LIGHT value of any particular sensing region changes from LIGHT=0 (beam blocked) in the immediately prior scan to a current LIGHT value of LIGHT=1 (beam detected), this indicates that the user removed a specimen holder from that particular sensing region after the prior complete optical scan. In the present example, processor 1505 determines that the LIGHT value of sensing region 1401-SR1 changes from LIGHT=1 to LIGHT=0, thus signifying the insertion of a specimen holder into sensing region 1401-SR1 which is under the A1 slot of specimen rack 100.

In response to determining via the optical scan that the user inserted a specimen holder in a sensing region such as sensing region 1401-SR1, processor 1505 conducts an RFID scan to determine the RFID of the newly added specimen holder in sensing region 1401-SR1. More particularly, processor 1505 initiates an RFID scan of the particular sensing regions in the same antenna zone as the antenna zone in which the newly added specimen holder was detected. In this example, the optical scan by processor 1505 determined that the newly inserted specimen holder is in sensing region 1401-SR1 which is in antenna zone 1, as seen in FIG. 16B. Sensing region 1401-SR1 exhibits a bold circle to indicate that it contains a specimen holder. In more detail, subsequent to the optical scan, processor 1505 accesses database 1511 to determine the particular antenna zone that includes the detected specimen holder. For the specimen holder in sensing region 1401-SR1, processer 1505 determines that the sensing region and specimen holder are in antenna zone 1, which is the selected antenna zone.

In response to this determination of antenna zone, processor 1505 initiates an RFID scan of the 18 sensing regions in antenna zone 1. Processor 1505 performs this RFID scan by instructing RFID reader 1522 to transmit an RFID interrogation signal to board 1102 via line 1552. The RF interrogation signal radiates to each of the sensing regions in antenna zone 1, namely sensing regions 1401-SR1 . . . 1401-SR9 and sensing regions 1402-SR1 . . . 1402-SR9. Each specimen holder in antenna zone 1 receives the RFID interrogation signal and in response transmits its respective RFID response signal, i.e. its RFID, back to RFID reader 1522. RFID reader 1522 detects these RFIDs in the RFID response signals, and provides the detected RFIDs to processor 1510. Processor 1505 accesses database 1511 and determines which one of the received RFIDs was not previously stored in database 1511. That particular new RFID is the RFID that corresponds to the newly detected specimen holder, namely the specimen holder in sensing region 1401-SR1 in this particular example. As seen in TABLE 2 above, processor 1505 updates database 1511 to now store the RFID unique identifier, namely 10110110, in the entry for the newly detected specimen holder in the sensing region 1401-SR1. Thus, the database entry for sensing region 1401-SR1 now includes the values LIGHT=0, RFID=10001001, and ANT ZONE=1 as shown in TABLE 2.

As discussed above, at some point in time prior to populating specimen rack 100 on specimen reader 1000 with specimen holders, a user or other entity places a unique RFID tag 115 and a unique optical barcode 120 on each specimen holder 110. Referring to FIG. 15, the user or other entity may use a dual RFID/barcode scanner 1592 to read the RFID and barcode of each specimen holder. Master database 1516 in host nonvolatile storage 1517 may include fields with entries that associate each RFID with a respective barcode. Processor 1505 may access master database 1516 to determine the barcode that corresponds to the RFID of a particular specimen holder. TABLE 3 below shows such an association between the RFID unique identifiers and barcode of representative specimen holders:

TABLE 3

| RFID | Optical Barcode |
|---|---|
| 10001001 | 411121 |
| 10001010 | 411122 |
| 10001011 | 411123 |
| 10001100 | 411124 |
| 10001101 | 411125 |
| 00001001 | 411126 |
| 00001010 | 411127 |
| 00001011 | 411128 |
| 00001100 | 411129 |
| 00001101 | 411130 |
| . | . |
| . | . |
| . | . |

In this manner, when processor 1505 determines that a specimen holder exhibiting a particular RFID resides at a particular sensing region and respective slot in specimen rack 100, processor 1505 may correlate that specimen holder with a optical barcode as well is RFID. Database 1511 may associate each sensing region and rack slot with values for LIGHT, RFID, ANTENNA ZONE and barcode. In the example of TABLE 2 wherein processor 1505 detects a specimen holder in sensing region 1401-SR1 and that specimen holder exhibits an RFID of 10001001, processor 1505 may access master database 1616, part of which is shown in TABLE 3 above, to determine the optical barcode that corresponds to that particular RFID. In the example of TABLE 2, processor 1505 determines that the barcode 411 121 corresponds to the RFID 10001001. Processor 1505 may store that barcode value locally in database 1511 along with the corresponding RFID as shown in the entry for sensing region 1401-SR1 in TABLE 2 above.

Thus, in one embodiment, database 1511 of specimen reader 1000 stores an RFID and a barcode for each slot of a particular specimen rack 100 on specimen reader 1000. Database 1511 may also store the RFID 125 of the particular specimen rack 100. During population of a particular specimen rack 100 with specimen holders one at a time, and/or after such population, specimen reader 1000 may upload database 1511 to host 1515. Host 1515 may transmit the contents of database 1511 to master database 1516 in nonvolatile storage 1517. In this manner, master database 1516 maintains a respective copy of database 1511 for each specimen rack 100 that specimen reader 1000 scans.

TABLE 4 below shows a representative example of master database 1516. In this simplified example, master database 1516 includes entries for two different specimen racks 100, namely a specimen rack 100 with an RFID=000000001 and a specimen rack with an RFID=000000002. In actual practice, master database 1516 may include entries for hundreds, thousands, tens of thousands or an even higher number of specimen racks 100. "N" represents the total number of specimen rack entries in master database 1516.

TABLE 4

| MASTER DATABASE RACK RFID = 000000001 | | | | |
|---|---|---|---|---|
| 1401-SR9/A9 | 1402-SR9/B9 | 1403-SR9/C9 | 1404-SR9/D9 | 1405-SR9/E9 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| 1401-SR3/A3 | 1402-SR3/B3 | 1403-SR3/C3 | 1404-SR3/D3 | 1405-SR3/E3 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| 1401-SR2/A2 | 1402-SR2/B2 | 1403-SR2/C2 | 1404-SR2/D2 | 1405-SR2/E2 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| 1401-SR1/A1 | 1402-SR1/B1 | 1403-SR1/C1 | 1404-SR1/D1 | 1405-SR1/E1 |
| LIGHT = 0<br>RFID = 10001001<br>BARCODE = 411 121<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| RACK RFID = 000000002 | | | | |
| 1401-SR9/A9 | 1402-SR9/B9 | 1403-SR9/C9 | 1404-SR9/D9 | 1405-SR9/E9 |
| LIGHT = 1<br>RFID = 0 | LIGHT = 1<br>RFID = 0 | LIGHT = 1<br>RFID = 0 | LIGHT = 1<br>RFID = 0 | LIGHT = 0<br>RFID = 00001010 |

TABLE 4-continued

MASTER DATABASE
RACK RFID = 000000001

| BARCODE = 0 | BARCODE = 0 | BARCODE = 0 | BARCODE = 0 | BARCODE = 411 127 |
| ANT ZONE = 1 | ANT ZONE = 1 | ANT ZONE = 2 | ANT ZONE = 2 | ANT ZONE = 3 |
| --- | --- | --- | --- | --- |
| 1401-SR3/A3 | 1402-SR3/B3 | 1403-SR3/C3 | 1404-SR3/D3 | 1405-SR3/E3 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| 1401-SR2/A2 | 1402-SR2/B2 | 1403-SR2/C2 | 1404-SR2/D2 | 1405-SR2/E2 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| 1401-SR1/A1 | 1402-SR1/B1 | 1403-SR1/C1 | 1404-SR1/D1 | 1405-SR1/E1 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 00001001<br>BARCODE = 411 126<br>ANT ZONE = 2 | LIGHT = 1<br>RFID = 0<br>BARCODE = 0<br>ANT ZONE = 3 |

.
.
.

RACK RFID = N

For simplicity, in the example of TABLE 4, the rack with an RFID=000000001, includes a single specimen holder, namely a specimen holder in sensing region 1401-SR1. The rack with an RFID=000000002 includes two specimen holders, namely a specimen holder in sensing region sensing region 1404-SR1 and a specimen holder in sensing region 1405-SR9.

In review, returning to TABLE 2 and FIG. 16B, the processor 1505 detected a specimen holder in sensing region 1401-SR1 using optical scanning in each of the sensing regions. More particularly, processor 1505 determined that an insertion change event occurred in sensing region 1401-SR1 by detecting that the LIGHT value of sensing region 1401-SR1 changed from LIGHT=1 (light beam detected) to LIGHT=0 (light beam blocked). In response to detection of this change event at sensing region 1401-SR1, processor 1505 initiates an RFID scan of the antenna zone in which sensing region 1401-SR1 is located, namely antenna zone 1. Processor 1505 initiates the RFID scan of antenna region 1 by instructing RFID reader 1522 to transmit an RF interrogation signal to the antenna of board 1102 via transmission line 1552. In response, each of the RFID tags of the specimen holders in antenna zone 1 transmits its respective RFID back to RFID reader 1522. RFID reader 1522 decodes the received RFIDs and sends the resultant RFID value to processor 1505. In this example, there is only one specimen holder in antenna zone 1, namely the specimen holder in sensing region 1401-SR1. Processor 1505 accesses local database 1511 to determine which RFID was added, or removed, to the specimen rack 100 that sits on specimen reader 1000. In the present example, processor 1505 determines that RFID 10001001 was added to the RFIDs that database 1511 stores for this particular specimen rack 100. Processor 1505 updates database 1511 to reflect that RFID 10001001 is now associated with sensing region 1401-SR1 and the corresponding rack slot A1 of specimen rack 100. TABLE 2 reflects this update of local database 1511 after detection of the specimen holder in sensing region 1401-SR1, while FIG. 16B graphically illustrates the current population of specimen rack 100 on specimen reader 1000. Processor 1505 may also access master database 1516 to determine the optical barcode that corresponds to RFID=10001001, namely optical barcode 411 121. Processor 1505 updates local database 1511 to reflect that the specimen holder in sensing region 1401-SR1 exhibits a LIGHT value of 0 (beam blocked), an RFID of 10001001, an optical barcode of 411 121 and an antenna zone=1.

Figure 16C:
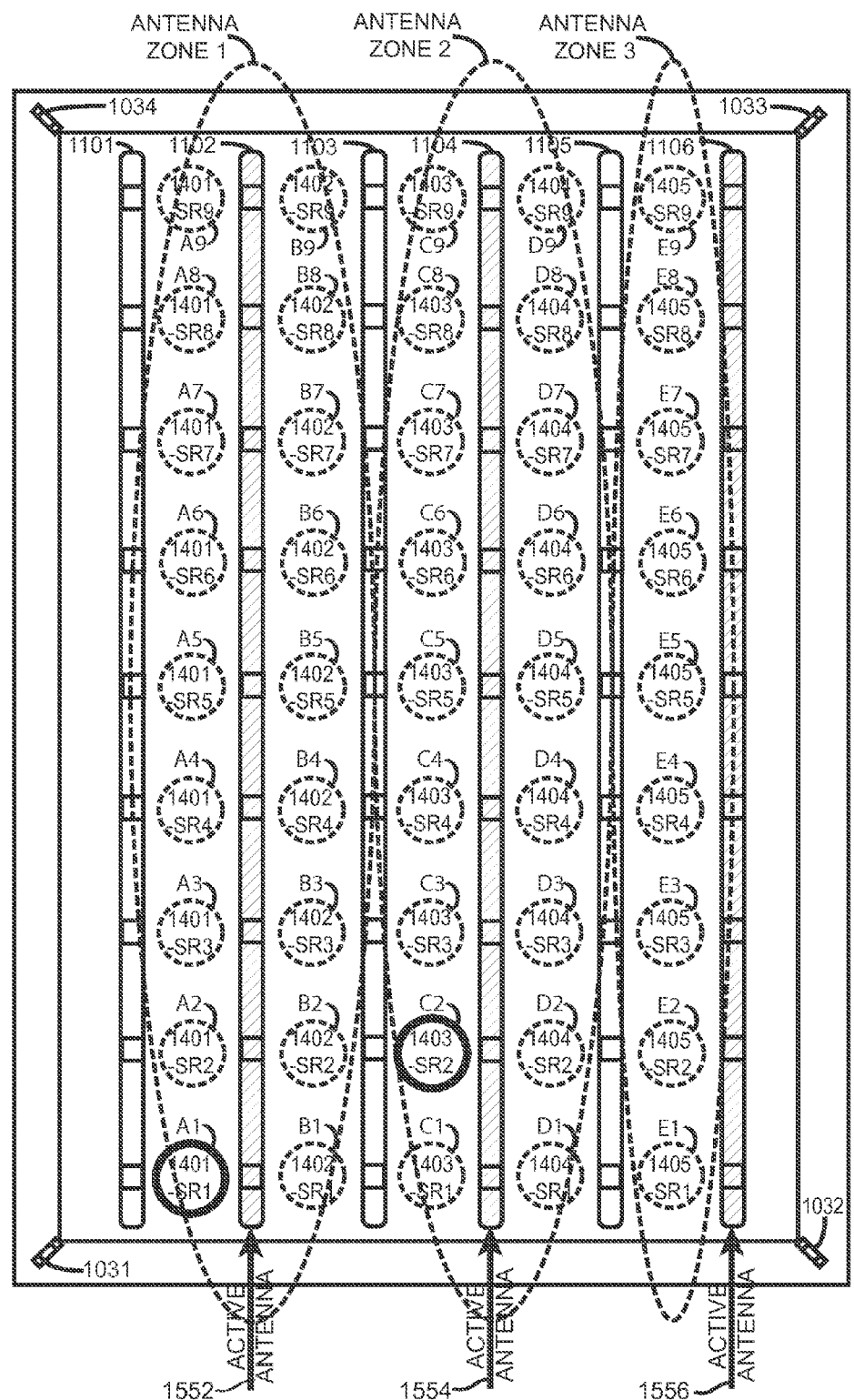
FIG. 16C is a top view of the disclosed specimen reader after populating the specimen rack with two specimen holders.

To further illustrate the operation of the disclosed specimen reader 1000 as the user adds more specimen holders to specimen rack 100, FIG. 16C shows specimen reader 1000 after the user adds a specimen holder to yet another sensing region of specimen reader 1000, namely to sensing region 1403-SR2 below specimen rack slot C2. Processor 1505 determines that the LIGHT value of sensing region 1403-SR2 changes from LIGHT=1 to LIGHT=0, thus signifying an insertion change event. namely an insertion of a specimen holder into sensing region 1403-SR2 which is under the C2 slot of specimen rack 100. Processor 1505 makes this determination of an insertion change event by accessing local database 1511 to determine at which sensing region the light value change from LIGHT=1 to LIGHT=0 since the last optical scan of the sensing regions by processor 1505.

In response to detection of this change event at sensing region 1403-SR2, processor 1505 initiates an RFID scan of the antenna zone in which sensing region 1403-SR2 is located, namely antenna zone 2. Processor 1505 initiates the RFID scan of antenna zone 2 by instructing RFID reader 1524 to transmit an RF interrogation signal to the antenna of board 1104 via transmission line 1554. In response, each RFID tag of each specimen holder in antenna zone 2 transmits their respective RFIDs back to RFID reader 1524. RFID reader 1524 decodes the received RFIDs and sends the resultant RFID values to processor 1505. In this example, there is now one (1) specimen holder in antenna zone 2, namely the specimen holder in sensing region 1403-SR2. For antenna zone 2, processor 1505 accesses local database 1511 to determine which RFID was added, or removed, to antenna zone 2 in the sensing regions of specimen reader 1000 below specimen rack 100. In the present example, processor 1505 determines that RFID 10001011 was added to the RFIDs that database 1511 stores for this particular specimen rack 100 as seen in Table 5 below. This signifies that the specimen holder in sensing region 1403-SR2 is the newly inserted specimen holder. Processor 1505 updates database 1511 to reflect that RFID 10001011 is now associated with sensing region 1403-SR2 and the corresponding rack slot A1 of specimen rack 100. TABLE 5 below reflects this update of local database entries after detection of the specimen holder in sensing region 1403-SR2, while FIG. 16C graphically illustrates the current population of specimen rack 100 on specimen reader 1000.

Figure 16D:
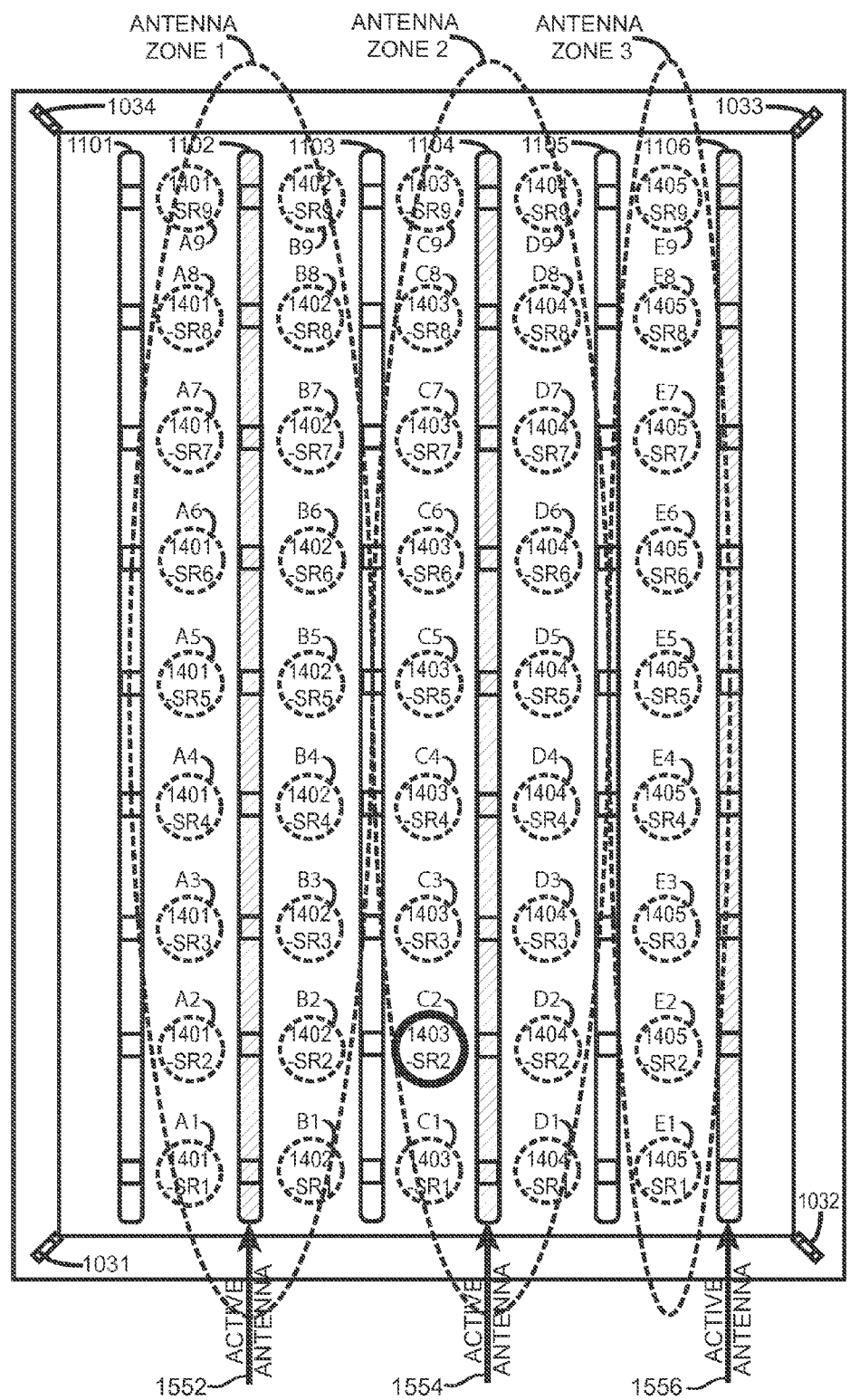
FIG. 16D is a top view of the disclosed specimen reader after removing one specimen holder from the specimen rack.

To still further illustrate the operation of the disclosed specimen reader 1000 as the user removes a specimen holder from specimen rack 100, FIG. 16D shows specimen reader 1000 after the user removes a specimen holder from a sensing region of specimen reader 1000, namely from sensing region 1401-SR1 below specimen rack slot A1. Processor 1505 determines that the LIGHT value corresponding to sensing region 1401-SR1 changes from LIGHT=0 (beam blocked) to LIGHT=1 (beam detected), thus signifying a "removal change event", namely a removal of a specimen holder from sensing region 1401-SR1. Processor 1505 makes this determination of a removal change event by accessing local database 1511 to determine at which sensing region the light value changes from LIGHT=0 (beam blocked) to LIGHT=1 (beam detected) since the last optical scan of the sensing regions by processor 1505.

In response to detection of this removal change event at sensing region 1401-SR1, processor 1505 updates local database 1511 to now reflect that LIGHT=1, thus indicating that no specimen holder is currently present in sensing region

TABLE 5

LOCAL DATABASE
TIME T = T1 (Insertion Change Event)

| 1401-SR9/A9 | 1402-SR9/B9 | 1403-SR9/C9 | 1404-SR9/D9 | 1405-SR9/E9 |
|---|---|---|---|---|
| LIGHT = 1<br>RFID = 0<br>BARCODE = 0<br>ANT ZONE = 1 | LIGHT = 1<br>RFID = 0<br>ANT ZONE = 1<br>BARCODE = 0 | LIGHT = 1<br>RFID = 0<br>ANT ZONE = 2<br>BARCODE = 0 | LIGHT = 1<br>RFID = 0<br>ANT ZONE = 2<br>BARCODE = 0 | LIGHT = 1<br>RFID = 0<br>ANT ZONE = 3<br>BARCODE = 0 |
| . . . | . . . | . . . | . . . | . . . |
| 1401-SR3/A3 | 1402-SR3/B3 | 1403-SR3/C3 | 1404-SR3/D3 | 1405-SR3/E3 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| 1401-SR2/A2 | 1402-SR2/B2 | 1403-SR2/C2 | 1404-SR2/D2 | 1405-SR2/E2 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 0<br>RFID = 10001011<br>BARCODE = 411 123<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| 1401-SR1/A1 | 1402-SR1/B1 | 1403-SR1/C1 | 1404-SR1/D1 | 1405-SR1/E1 |
| LIGHT = 0<br>RFID = 10001001<br>BARCODE = 411 121<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |

Processor 1505 may also access master database 1516 to determine the optical barcode that corresponds to RFID=10001011, namely optical barcode 411 123. As seen in Table 5 above, processor 1505 updates local database 1511 to reflect that the specimen holder in sensing region 1403-SR2 exhibits a LIGHT value of 0 (beam blocked), an RFID of 10001011, an optical barcode of 411 123 and an antenna zone=2. In the example above, 10001011 is the RFID unique identifier of the particular RFID.

1401-SR1 and the corresponding rack slot A1 of specimen rack 100. Processor 1505 also updates local database 1505 to now reflect that RFID=0, thus indicating that no RFID is currently associated with sensing region 1401-SR1 and the corresponding rack slot A1 of specimen rack 100. TABLE 6 below reflects this update of local database entries after detecting removal of the specimen holder in sensing region 1401-SR1, while FIG. 16D graphically illustrates the current population of specimen rack 100 on specimen reader 1000.

TABLE 6

LOCAL DATABASE
TIME T = T1 (Insertion Change Event)

| 1401-SR9/A9 | 1402-SR9/B9 | 1403-SR9/C9 | 1404-SR9/D9 | 1405-SR9/E9 |
|---|---|---|---|---|
| LIGHT = 1<br>RFID = 0<br>BARCODE = 0<br>ANT ZONE = 1 | LIGHT = 1<br>RFID = 0<br>ANT ZONE = 1<br>BARCODE = 0 | LIGHT = 1<br>RFID = 0<br>ANT ZONE = 2<br>BARCODE = 0 | LIGHT = 1<br>RFID = 0<br>ANT ZONE = 2<br>BARCODE = 0 | LIGHT = 1<br>RFID = 0<br>ANT ZONE = 3<br>BARCODE = 0 |
| . . . | . . . | . . . | . . . | . . . |
| 1401-SR3/A3 | 1402-SR3/B3 | 1403-SR3/C3 | 1404-SR3/D3 | 1405-SR3/E3 |
| LIGHT = 1<br>RFID = 0<br>BARCODE = 0<br>ANT ZONE = 1 | LIGHT = 1<br>RFID = 0<br>BARCODE = 0<br>ANT ZONE = 1 | LIGHT = 1<br>RFID = 0<br>BARCODE = 0<br>ANT ZONE = 2 | LIGHT = 1<br>RFID = 0<br>BARCODE = 0<br>ANT ZONE = 2 | LIGHT = 1<br>RFID = 0<br>BARCODE = 0<br>ANT ZONE = 3 |
| 1401-SR2/A2 | 1402-SR2/B2 | 1403-SR2/C2 | 1404-SR2/D2 | 1405-SR2/E2 |
| LIGHT = 1<br>BARCODE = 0<br>RFID = 0<br>ANT ZONE = 1 | LIGHT = 1<br>BARCODE = 0<br>RFID = 0<br>ANT ZONE = 1 | LIGHT = 0<br>10001011<br>RFID =<br>BARCODE =<br>411 123<br>ANT ZONE = 2 | LIGHT = 1<br>BARCODE = 0<br>RFID = 0<br>ANT ZONE = 2 | LIGHT = 1<br>BARCODE = 0<br>RFID = 0<br>ANT ZONE = 3 |
| 1401-SR1/A1 | 1402-SR1/B1 | 1403-SR1/C1 | 1404-SR1/D1 | 1405-SR1/E1 |
| LIGHT = 1<br>BARCODE = 0<br>RFID = 0<br>ANT ZONE = 1 | LIGHT = 1<br>BARCODE = 0<br>RFID = 0<br>ANT ZONE = 1 | LIGHT = 1<br>BARCODE = 0<br>RFID = 0<br>ANT ZONE = 2 | LIGHT = 1<br>BARCODE = 0<br>RFID = 0<br>ANT ZONE = 2 | LIGHT = 1<br>BARCODE = 0<br>RFID = 0<br>ANT ZONE = 3 |

Returning to FIG. 15, an audio alert 1594 operatively couples to processor 1505 to provide the user with an audio cue that specimen reader 1000 has properly read the RFID of a specimen holder inserted into a slot of specimen rack 100 on specimen reader 1000. In another embodiment, a visual indicator 1596, such as a bi-color LED (red/green), operatively couples to processor 1505 to provide the user with a visual cue that specimen reader 1000 has properly read the RFID of a specimen holder inserted into a slot in specimen rack 100 of specimen reader 1000. The user places specimen holders one at a time into specimen rack 100 on the specimen reader 1000. When the user places a specimen holder into a particular rack slot and corresponding sensing region, processor 1505 optically detects the newly inserted specimen holder in the manner discussed above. In response to optically detecting the presence of the newly inserted specimen holder, processor 1505 sends an RF interrogation signal to the particular antenna zone that includes the newly inserted specimen holder. If processor 1505 successfully determines the RFID of the newly inserted specimen holder, then processor 1505 instructs audio alert 1594 to sound one of two different tones. A high frequency tone, i.e. a happy beep, indicates to the user that specimen reader 1000 properly read the RFID of the newly inserted specimen holder. A low frequency tone or buzz, i.e. an error beep, indicates a read error to inform the user that specimen reader 1000 did not properly read the RFID of the newly inserted specimen holder. For successful reads of the RFID of the newly inserted specimen holder, processor 1505 may also instruct the visual indicator LED 1596 to display a green light. In the event of an unsuccessful RFID read, then processor 1505 instructs the visual indicator LED 1596 to display a red light to indicate read failure. In the event of read failure, the user may rotate the specimen holder in a particular rack opening until specimen reader 1000 properly reads the RFID of the newly inserted specimen holder.

FIG. 17 is a flowchart that depicts a simplified embodiment of the disclosed methodology for initially populating specimen rack 100 with specimen holders. Before discussing this process flow, it is again noted that the term "slot" is a short-hand term for the openings in specimen rack 100, wherein the openings may each receive a respective specimen holder. The specimen holder receiving region below each rack opening forms part of each rack slot. When the user or other entity places specimen rack 100 on specimen reader 1000, each sensing region of the specimen reader 1000 corresponds to a respective slot of specimen rack 100. Specimen rack 100 includes a specimen holder receiving region below each opening. By way of review, specimen rack 100 includes a slot A1 that includes a specimen receiving region A1' extending below the opening of slot A1. The rack opening and specimen receiving region together form a slot into which a specimen holder is inserted. In this particular example, sensing region 1401-SR1 of specimen reader 1000 corresponds to the slot A1. In other words, sensing region 1401-SR1 is coextensive with and/or aligns with slot A1 to enable specimen reader 1000 to optically scan the specimen holder slot A1.

In the initial population process, process flow commences at START block 1700. The user or other entity applies an optical barcode 120 to the specimen holder 105, as per block 1705. The user or other entity also applies an RFID tag 115 to the specimen holder 105, as per block 1710. Dual RFID/barcode scanner 1592 scans the RFID tag of specimen holder 105 to determine the RFID thereof, and further scans the optical barcode 120 to determine the barcode of specimen holder 105. In one embodiment, processor 1505 associates the RFID and barcode of each specimen holder and stores the associated RFID and barcode in a database, such as local database 1511 and/or master database 1516, as per block 1720.

Processor 1505 continuously optically scans the sensing regions of specimen reader 1000, each sensing region being associated with a respective rack slot of specimen rack 100, as per block 1725. In other words, specimen reader 1000 may optically scan all 45 sensing regions of the specimen reader serially, one at a time, and then repeats the scan of the 45 sensing regions until it detects a change event such as the insertion or removal of a specimen holder from the specimen rack. The user or other entity inserts a specimen holder in a particular open slot of the specimen rack. The specimen reader sensing region corresponding to this particular rack slot receives the specimen holder, as per block 1730. As mentioned above with respect to block 1725, processor 1505 continuously optically scans the sensing regions to determine a change event. Processor 1505 conducts a test for each sensing region by optically scanned each sensing region to determine if a change event occurs at such sensing region, as per decision block 1735. If processor 1505 does not detect such a change event, then process flow continues back to block 1725 and optical scanning of the 45 sensing regions continues. However, if processor 1505 does detect a change event, then processor 1505 updates the database to reflect the sensing region and rack slot where the change event occurred. Processor 5005 may store this information in local database 1511 and/or master database 1516, as per block 1740.

After optically detecting a change event and updating the database to reflect the change event, processor 1505 turns on an antenna within range of the slot location of the change event and transmits an RFID interrogation signal thereto, as per block 1745. For example, if a particular specimen reader 1000 includes multiple antenna zones such as antenna zone 1, and antenna zone 2 and antenna zone 3 and the change event occurred in antennas zone 1, then processor 1505 transmits the RFID interrogation signal to antenna zone 1, as per block 1745. In response to the RFID interrogation signal, any RFID tags on specimen holders within antenna zone 1 transmit their respective RFID's. Processor 1505 detects all of these RFID's transmitted from the specimen holders in antenna zone 1, as per block 1750. Processor 1505 accesses the database to compare the RFID's currently received from antennas zone 1 with RFID's received in a prior scan, if any, as per block 1755. As part of this comparison, processor 1505 determines any new RFID's, i.e. RFID's that were not received in any previous RF scan. Processor 1505 stores the new RFID in the database together with the corresponding sensing region and rack slot location corresponding to that new RFID, as per block 1760. This new RFID is the RFID of the newly inserted specimen holder. Processor 1505 may access master database 1516 to determine the optical barcode that is associated with the new RFID. Processor 1505 stores the optical barcode together with the new RFID in local database 1511 and/or master database 1516.

Processor 1505 determines if the process ends, as per decision block 1770. For example, the user may remove specimen rack 100 from specimen reader 1000. Whereas prior to such removal, processor 1505 detects the particular RFID tag 115 associated with specimen rack 100, upon RFID interrogation thereof after such removal, processor 1505 will no longer detect the presence of RFID tag 115. Processor 1505 may interpret this as the end of the population process and in response process flow continues to END block 1775. However, if specimen rack 100 is still present on specimen reader 1000 such that processor 5005 still detects the presence of the RFID tag 125 of the specimen rack 100, then the process continues. For example, process flow may continue back to block 1705 were another specimen holder is prepared for insertion in specimen rack 100. Alternatively, if the next-to-be-inserted specimen holder already includes an optical barcode and RFID tag, then process flow may continue directly to block 1715 wherein the user or other entity uses the dual RFID/barcode reader to determine the RFID and optical barcode of the next-to-be-inserted specimen holder.

Figure 18:
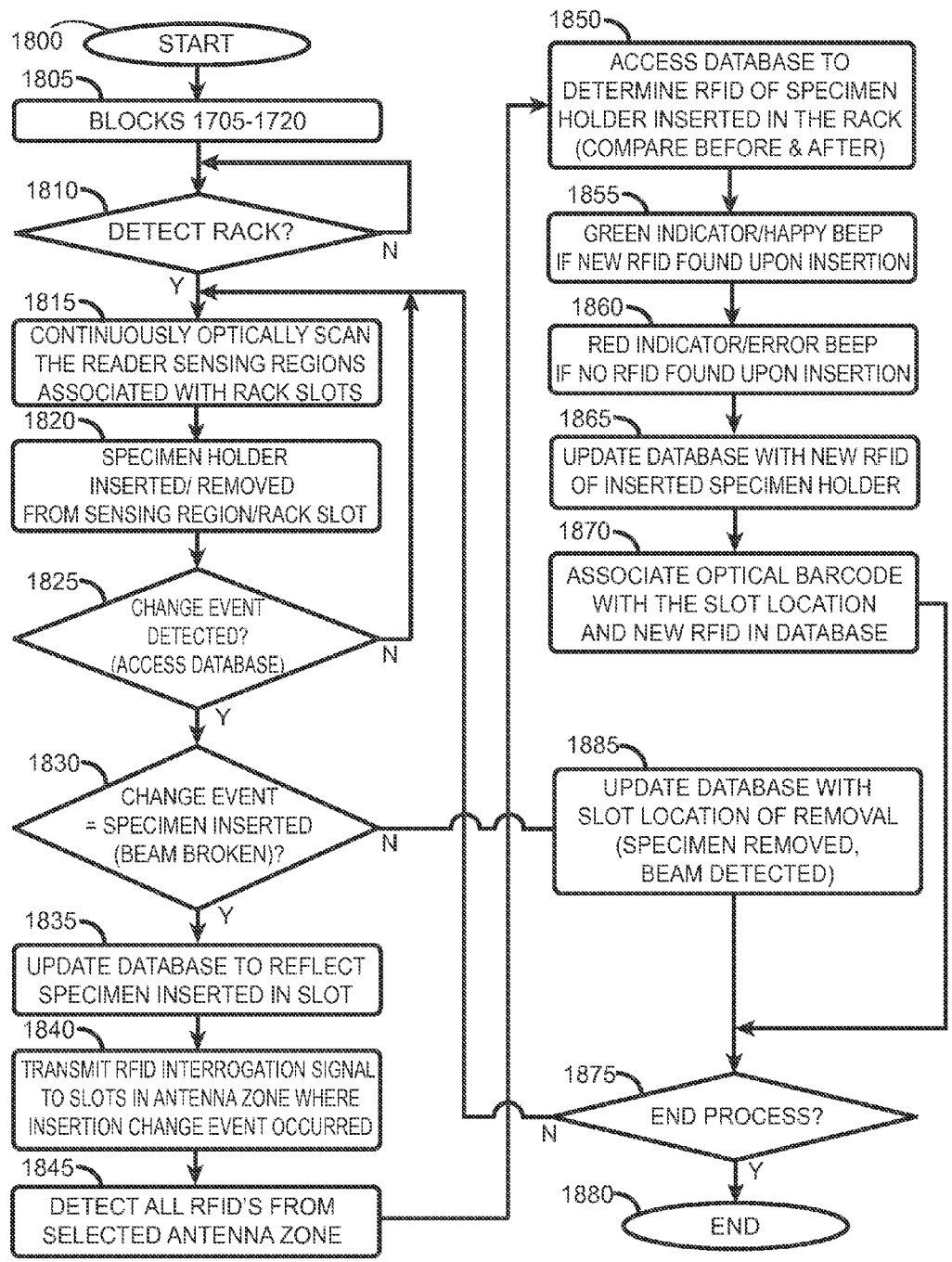
FIG. 18 is a flowchart of the disclosed process for both inserting specimen holders into, and removing specimen holders from, the disclosed specimen rack on the specimen reader.

FIG. 18 is a more detailed flowchart that describes process flow in one embodiment of the disclosed methodology of using specimen reader 1000 to inventory specimen holders. As part of this process, the user or other entity inserts specimen holders into specimen rack 100 or removes specimen holders from specimen rack 100. Process flow commences at START block 1800. Blocks 1705-1720 involve reading the RFID tag and optical barcode of each specimen holder that specimen reader 1000 will receive, as already described above. The host 1515 may associate each RFID with a respective optical barcode in master database 1516, as discussed above in more detail. The user places specimen rack 100 on specimen reader 1000. In this embodiment, the user inserts specimen holders into, or removes specimen holders from, specimen rack 100 one at a time. Processor 1505 continuously scans for a rack RFID tag such as RFID tag 125. This enables specimen reader 1000 to detect the presence of a specimen rack 100 on reader 1000. In one embodiment, RFID tags exhibiting a particular range of values may be reserved for identifying specimen racks, whereas other ranges of RFID values may be dedicated to specimen holders. In this manner, processor 1505 may readily distinguish between a specimen rack RFID and a specimen holder RFID. Using this approach, processor 1505 conducts a test at test block 1810 to determine if a specimen rack 100 is present on specimen reader 1000. If processor 1505 does not identify a specimen rack in decision block 1810, then processor 1505 continues scanning for a rack RFID. However, if processor 1505 detects the presence of a rack 100 by sensing its special rack RFID, then processor 1505 commences continuous optical scanning of the sensing regions associated with the rack slots of specimen rack 100. The user may insert a specimen holder into, or remove a specimen holder from, a particular sensing region/rack slot, as per block 1820. It is noted again that each sensing region of specimen reader 1000 corresponds to a respective rack slot of specimen rack 100.

Processor 1505 performs a test to detect change events at each sensing region/rack slot, as per decision block 1825. In one embodiment, the user may add specimen holders to the specimen rack, one specimen holder at a time. Alternatively, the user may remove specimen holders from the specimen rack, one specimen holder at a time. Thus, in any particular optical scan of the 45 sensing regions, processor 1505 should detect at most one change event. Processor 1505 performs change event detection by optically scanning the sensing regions and accessing database 1511. More particularly, processor 1505 optically scans all 45 sensing regions/rack slots and determines those that a specimen holder occupies and those that specimen holders do not currently occupy. Processor 1505 accesses database 1511 to determine those particular sensing regions/rack slots for which a change event occurs, namely changing from a specimen holder detected to specimen holder not detected value (a removal change event) or from a specimen holder not detected to a specimen holder detected value (an insertion change event). If processor 1505 does not detect a change event at decision block 1825, process flow continues back to block 1815 and processor 1505 continues optically scanning the sensing regions of the specimen reader 1000.

However, if processor 1505 does successfully detect a change event at a particular sensing region/rack slot, then processor 5005 performs a test to determine if the particular change event is an insertion change event or a removal change event, as per decision block 1825. To perform this determination, processor 1505 accesses the database 1511 to determine if, for each sensing region, the current value of LIGHT changed from the value of LIGHT in the immediately prior scan. If the value of LIGHT changed from LIGHT=1 (light detected) to LIGHT=0 (light blocked) this indicates a change event, namely an insertion change event. In this case, the specimen holder is blocking the light beam at the sensing region. However, if the value of LIGHT changed from LIGHT=0 (light blocked) to LIGHT=1 (light detected), this indicates a removal change event because no specimen holder is present to block the light beam at the sensing region. Processor 1505 performs a test to determine if a detected change event is a specimen inserted change event, as per decision block 1830.

If processor 1505 determines at decision block 1830 that the change event is a specimen inserted change event, then processor 1505 updates database 1511 to reflect the current status of the affected sensing region/rack slot, as per block 1835. In other words, processor 1505 updates the entry for the particular sensing region/rack slot to indicate that there is now a specimen holder at that particular sensing region/rack slot, as per block 1835. In response to detecting an insertion change event at decision block 1830 and updating database 1511 to reflect the change at block 1835, processor 1505 instructs an appropriate one of the RFID readers to transmit an RFID interrogation signal to the particular antenna zone for which the processor found an insertion change event, i.e. the selected antenna zone, as per block 1840. Any specimen holders in this particular antenna zone respond back by transmitting respective unique RFIDs to the RFID reader and processor 1505. The RFID reader receives the RFIDs from these specimen holders in the particular antenna zone and detects the RFIDs from the particular antenna zone, as per block 1845.

Processor 1505 determines the particular RFID that corresponds to the newly-inserted specimen holder by accessing database 1511 and/or master database 1516, as per block 1850. Processor 1505 compares a list of currently received RFIDs for the selected antenna zone with the RFIDs previously stored by the database for that particular antenna zone. Processor 1505 determines the particular RFID for which the processor observes as change, i.e. an insertion or removal. If processor 1505 finds a newly added RFID that was not previously detected for this antenna zone, then this particular newly added RFID is the RFID of the specimen holder that the user inserted into the rack. If processor 1505 is successful in optically scanning for the newly added specimen holder and successful in identifying the RFID for that newly added specimen, then processor 1505 instructs audio alert 1594 to play a high frequency audio sound, and further instructs LED 1596 to emit a green light, to indicate a successful read to the user, as per block 1855. However, if processor 1505 successfully detects a newly inserted specimen holder via optical scanning, but does not also detect a newly added RFID, then processor 1505 instructs audio alert 1594 to play a low frequency audio sound or error tone, and further instructs LED 1596 to emit a red light, to indicate an unsuccessful RFID read to the user with respect to the newly inserted specimen holder, as per block 1860.

Upon successfully optically detecting a newly inserted specimen holder at a particular sensing region/rack slot and successfully detecting the corresponding RFID for the newly inserted specimen holder at that sensing region/rack slot, processor 1505 updates database 1511 and/or master database 1516 to reflect that this particular sensing region/rack slot now has a particular specimen holder inserted therein and further updates the database to include the RFID that corresponds to the newly inserted specimen holder, as per block 1865. Processor 1505 further accesses the database to determine the barcode of the detected specimen holder. In other words, knowing the RFID of the newly detected specimen holder, processor 1505 access the database to determine the particular optical barcode that corresponds to this RFID. Processor 1505 associates the optical barcode of the newly inserted specimen holder with the sensing region/rack slot of the newly inserted specimen holder, as per block 1870

Specimen reader performs a test to determine if the population process should now end, as per decision block 1875. To make this determination, specimen reader 1000 may detect when the user removes the specimen rack 100 from the specimen reader 1000. One way to make this determination of the end of the population process is that processor 1505 periodically perform RFID scans of RFID 125 to determine if the particular specimen rack is still present atop specimen reader 1000. If the user removes the specimen rack, processor 1505 will detect that RFID is now longer present. In response to this detection that the RFID of the specimen rack is now longer present, processor 1505 may interpret this a request for end-of-process, and process flow ends at end block 1880. However if processor 1505 still detects the presence of the RFID tag 125, then processor 1505 may interpret this as indicating that the process should not end. Consequently, processor 1505 returns to its task of continuously optically scanning the reader sensing regions for a change event, as per block 1815.

The discussion above refers to the detection and handling of specimen insertion change events, namely when processor 1505 detects the blocking of the light beam at a particular sensing region/rack slot where no such blocking existed in the immediately prior optical scan. As discussed above, when processor 1505 detects such a change event, i.e. wherein the beam is now blocked, then process flow continues to block 1835 as already discussed. However, if processor 1505 detects a change event, as per decision block 1825, and if processor 1505 further determines that this change event involves means that processor 1505 detected a removal change event. In response to detection of such a removal change event, processor 1505 updates database 1511 to record such a removal change event, as per block 1885. The process may continue or end, as per decision block 1875.

Figure 19A:
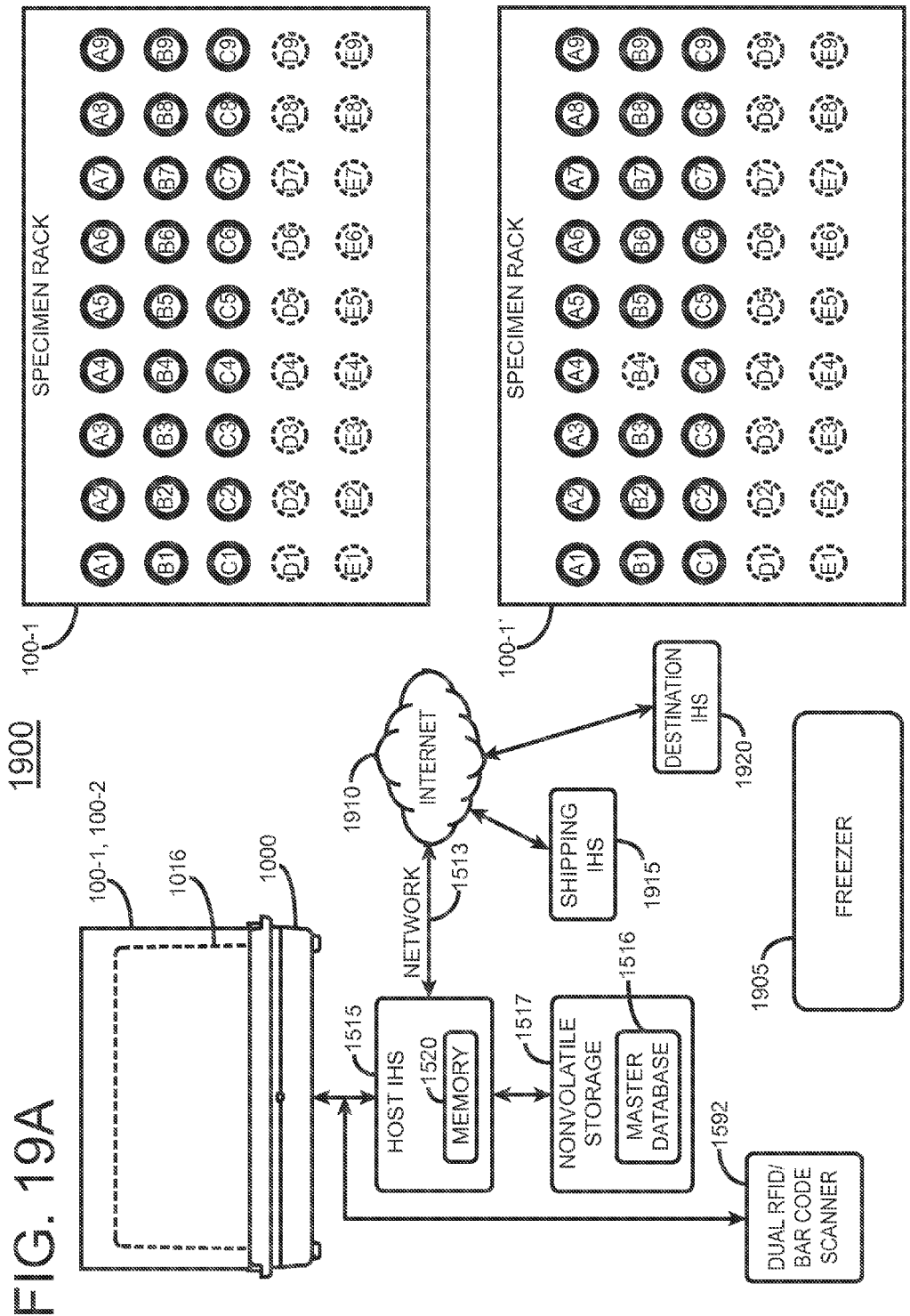
FIG. 19A is a block diagram of one embodiment of the specimen holder tracking system that illustrates specimen removal from a specimen rack.

FIG. 19A is a block diagram of a representative specimen holder tracking system 1900 including specimen reader 1000 and specimen rack 100-1. Specimen rack 100' shows specimen rack 100 after removal of a specimen holder from rack slot B4. Tracking system 1900 may track specimen holders removed from specimen rack 100-1 and inserted into another specimen rack 100-2 that is shown in FIG. 19B. As seen in FIG. 19A, specimen rack 100-1 includes rack slots A1, A2, . . . A9, rack slots B1, B2, . . . B9, rack slots C1, C2, . . . C9, rack slots D1, D2, . . . D9, and rack slots E1, E2, . . . E9. Those rack slots that are empty are drawn as dashed circles. Those rack slots that are populated with a specimen holder are drawn as bold circles. Specimen holder tracking system 1900 includes one or more freezers 1905. Objects are not drawn to scale in FIGS. 19A and 19B. Representative freezer 1905 may store multiple specimen holder racks such as specimen holder racks 100-1 and 100-2. A specimen rack 100-1 is situated on specimen reader 1000 as shown in FIG. 19A. FIG.

19A uses a dashed line in specimen reader 100 is used to represent sensor housing 1016 that is covered by specimen rack 100-1.

Specimen reader 1000 couples to a host information handling system (IHS) 1515 that may include a memory 1520. Host IHS 1515 couples to nonvolatile storage 1517 that stores a master database 1516. In one embodiment, nonvolatile storage 1517 and master database 1516 may be internal to host IHS 1515. A dual RFID/barcode scanner 1592 couples to host IHS 1515. A network 1513 couples via the Internet 1910 or other communication network to a shipping IHS 1915 and a destination IHS 1920. After scanning the specimens of a specimen rack and automatically entering a particular specimen holder's RFID unique identifier and associated barcode and associated rack slot unique identifier into master database 1515, the user may desire to ship this inventoried specimen rack to another user at a destination, as discussed below in more detail.

FIG. 19A shows a partially populated specimen rack 100-1 including specimen holders in rack slots A1, A2 . . . C9, as indicated by bold solid circles. Rack slots D1, D2 . . . E9 of specimen rack 100-1 are unpopulated, as indicated by dashed circles. For purposes of discussion, assume that tracking system 1900 previously inventoried the specimen holders in the specimen rack 100-1 in accordance with the teachings above. Thus, for each rack slot that stores a specimen holder, master database 1516 stores an RFID unique identifier and an associated barcode unique identifier for the specimen holder as well as the corresponding rack slot unique identifier for that specimen holder. When a user removes a specimen holder such as the specimen holder in rack slot B4, tracking system 1900 automatically optically detects the removal of the specimen holder from the specimen rack and updates master database 1516 accordingly. Subsequent to removal of the specimen holder in rack slot B4, specimen rack 100-1 appears as shown in specimen holder 100-1' in FIG. 19A. In other words, when a user removes the specimen holder in rack slot B4 from specimen rack 100-1, specimen reader 100 optically detects a removal change event at rack slot B4. Specimen reader 100 updates master database 1516 to reflect that there is now no specimen holder in rack slot B4. Master database 1516 removes the association between the rack slot identifier of rack slot B4 and the RFID unique identifier and barcode unique identifier of the newly removed specimen holder.

For discussion purposes, assume that the user moves the newly removed specimen holder to specimen rack 100-2 after placing specimen rack 100-2 on specimen reader 1000, as shown in FIG. 19B. FIG. 19B shows specimen rack 100-2 as the specimen rack would appear prior to insertion of the specimen holder in specimen rack 100-2. FIG. 19B also shows specimen rack 100-2' as the specimen rack would appear after insertion of the specimen holder as a newly inserted specimen holder. In this particular example, the user inserts the specimen holder in rack slot C2 as shown by specimen holder 100-2'. Specimen reader 1000 optically detects an insertion change event at rack slot C2. In response to detecting the insertion change event at rack slot C2, specimen reader 1000 determines the RFID unique identifier and barcode unique identifier associated with this particular specimen holder which is now designated the newly inserted specimen holder. Specimen reader 1000 updates master database 1516 to store the rack slot identifier of the newly inserted specimen holder at rack slot C2 with the RFID unique identifier and barcode unique identifier of the newly inserted specimen holder all in association with one another. In this manner the rack slot identifier of the rack slot C2 associates with both RFID unique identifier and the barcode unique identifier of the newly inserted specimen holder.

After the population of specimen rack 100-2 with specimen holders, master database 1516 includes entries for each specimen holder in that rack. That entry may include the rack slot identifier, the RFID unique identifier and the barcode unique identifier associated with a particular specimen holder. Each entry may be cross indexed to an associated patient number or other identification number. In practice, master database 1516 may include entries for the specimen holders in a very large number of specimen racks, for example hundreds, thousands and even more storage racks. This enables a user to submit a query to master database 1516 for a particular patient number or other identification number as input. In response to the query, host IHS 1515 may search through the entries of master database 1516 to locate all specimen holders that correspond to a particular patient number or other number. Host IHS 1515 may display responsive results on display 1598 of FIG. 15. The responsive results may include the RFID unique identifier and the actual physical location of the particular specimen rack that includes the specimen holder that is the target of the search. The responsive results may also include the RFID unique identifier and the barcode unique identifier of the particular specimen holder that is the target of the search.

In one scenario, the user may want to ship a specimen rack including multiple specimen holders to a particular destination at which a destination IHS 1920 is located. The destination may be another laboratory, hospital, medical storage facility, business organization, governmental organization or other business or non-business entity. Host IHS 1515 may communicate with destination IHS 1920 via network 1513 and the Internet 1910. Host IHS 1515 may also communicate with a shipping IHS or shipping IHSS 1915 at one or more shipping companies. As part of the process of shipping a specimen rack to a particular destination, the user may obtain a shipping number from shipping IHS 1915 by submitting an appropriate request on host IHS 1515 and sending the request to shipping IHS 1915. Shipping IHS 1915 responds with a unique shipping number. Master database 1516 may associate this shipping number with the specimen rack RFID unique identifier as well as the RFID unique identifiers and barcode unique identifiers of the specimen holders that the user is planning to send to the destination. The user may send all of this information to the destination IHS so that a user at the destination IHS is aware of the precise contents of the specimen rack being shipped as will as the shipping number for that shipment.

More generally, the user may submit a query to master database 1516 at any time to determine the location of any specimen holder in any specimen rack that tracking system 1900 has inventoried. The user may search by any searching term for which the database is indexed. For example, the user query may specify a patient number, rack RFID unique identifier, specimen holder RFID unique identifier, barcode unique identifier or other search terms as well. Host IHS 1515 may graphically display search results to the user to enable the user to quickly determine the actual physical location of the specimen holder or specimen holders that are the target of the search.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

What is claimed is:

1. A specimen rack, comprising:
  a foldable box that is moveable between an open position and a closed position, the foldable box including an open top and an open bottom when the foldable box is in the open position; and
  a removable insert member situated adjacent the open top of the foldable box when the foldable box is in the open position, the removable insert member including a plurality of specimen holder receiving slots for receiving specimen holders for specimen storage.

2. The specimen rack of claim 1, further comprising an RFID tag situated on the foldable box.

3. The specimen rack of claim 1, further comprising an RFID tag situated on the removable insert member.

4. The specimen rack of claim 1, wherein the removable insert member includes a plurality of tabs that fit in a plurality of corresponding apertures in the foldable box to support the removable insert member in the foldable box.

5. The specimen rack of claim 1, wherein the removable insert member includes first and second handles situated on opposed ends of the removable insert member, the first and second handles extending through respective first and second apertures on opposed ends of the foldable box.

6. The specimen rack of claim 5, wherein the first and second handles include first and second inner flaps that removably adhesively attach to the foldable box.

7. The specimen rack of claim 1, wherein the plurality of specimen holder receiving slots are arranged in rows and columns.

8. The specimen rack of claim 1, further comprising a protective sleeve that slides over the foldable box.

9. The specimen rack of claim 1, wherein the specimen rack is made of cardboard.

10. The specimen rack of claim 1, wherein the specimen rack is made of chipboard.

11. The specimen rack of claim 1, wherein a specimen holder is situated in at least one of the specimen holder receiving slots of the removable insert member.

12. A method of assembling a specimen rack, comprising:
  providing a foldable box that is moveable between a closed open position and an position, the foldable box including an open top and an open bottom when the foldable box is in the open position;
  moving the foldable box from the closed position to the open position;
  attaching a removable insert member adjacent the open top of the foldable box when the foldable box is in the open position, the removable insert member including a plurality of specimen holder receiving slots for receiving specimen holders for specimen storage.

13. The method of claim 12, wherein the removable insert member includes a plurality of tabs that fit in a plurality of corresponding apertures in the foldable box to support the removable insert member in the foldable box, the method including inserting the plurality of tabs respectively in the plurality of apertures of the foldable box.

14. The method of claim 12, wherein the removable insert member includes first and second handles situated on opposed ends of the removable insert member, the method including inserting the first and second handles to extend through first and second apertures, respectively, on the opposed ends of the foldable box.

15. The method of claim 14, wherein the first and second handles include first and second inner flaps, respectively, the method including removably adhesively attaching the first and second inner flaps to the foldable box.

16. The method of claim 12, further comprising sliding a protective sleeve over the foldable box and the removable insert member.

* * * * *